US006476070B2

(12) United States Patent
Krall et al.

(10) Patent No.: US 6,476,070 B2
(45) Date of Patent: *Nov. 5, 2002

(54) COMPOSITIONS USEFUL FOR REMODELING BODY SPACES

(75) Inventors: Robert E. Krall, Alpine, CA (US); Charles W. Kerber, La Mesa, CA (US); Kimberly Knox, La Mesa, CA (US)

(73) Assignee: Provasis Therapeutics Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/497,075

(22) Filed: Feb. 2, 2000

(65) Prior Publication Data

US 2002/0141969 A1 Oct. 3, 2002

Related U.S. Application Data

(63) Continuation-in-part of application No. 09/241,368, filed on Jan. 29, 1999, and a continuation of application No. 09/151,621, filed on Sep. 11, 1998, now Pat. No. 6,037,366.
(60) Provisional application No. 60/058,510, filed on Sep. 11, 1997.

(51) Int. Cl.$^7$ .................. A61K 31/26; A61K 31/00; A61K 33/00; A61K 47/00; A61K 49/04
(52) U.S. Cl. .................. 514/527; 424/9.4; 424/9.41; 424/9.411; 424/9.42; 424/78.08; 424/78.31; 424/78.39; 424/78.37; 424/422; 424/423; 424/605; 424/617; 424/649; 424/667; 424/672; 514/492; 514/495; 514/526; 514/529; 514/690; 514/718; 514/730; 514/731; 514/769; 514/772; 514/772.3; 514/772.4; 514/783; 514/785; 514/788; 514/970
(58) Field of Search ................... 424/9.4, 9.42, 424/78.31, 78.34, 78.35, 78.37, 462, 649, 667, 723, 9.41, 9.411, 78.08, 78.39, 422, 423, 605, 617, 672; 514/772.3, 772.4, 772.6, 492, 495, 526, 527, 529, 690, 718, 730, 731, 769, 772, 783, 785, 788, 970

(56) References Cited

U.S. PATENT DOCUMENTS

| | | | |
|---|---|---|---|
| 4,359,454 A | 11/1982 | Hoffman | |
| 4,713,235 A | 12/1987 | Krall | |
| 5,328,687 A | 7/1994 | Leung et al. | |
| 5,695,480 A | 12/1997 | Evans et al. | |
| 5,795,331 A | 8/1998 | Cragg et al. | 604/103.01 |
| 5,981,621 A | 11/1999 | Clark et al. | |
| 6,037,366 A * | 3/2000 | Krall et al. | 514/527 |

FOREIGN PATENT DOCUMENTS

EP    0 747 069 A2    11/1996

OTHER PUBLICATIONS

Woodward, 'Physiological and biochemical evaluation of implanted polymers' (Ann. N. Y. Acad. Sci. (1968), vol. 146, No. 1, pp. 225–250), STN/CAS online, file CAPLUS, Abstract.*

Mathis et al.,AJNR Am J Neuroradiol (1997), vol. 18, pp. 1087–1091.*

Almen, et al., "Radiocontrast agents" *Basic Methods of Investigative Neuroradiology*, 1984, pp. 348 and 363.

Tseng, et al., "Modified ethoxyethyl cyanoacrylate for therapeutic embolization of arteriovenous malformations", *Journal of Biomedical Material Research*, vol. 24, (1990), pp. 65–77.

Stephen C. Woodward, "Physiological and biochemical evaluation of implanted polymers", *Ann. N.Y. Acad. Sci.*, (1968), 2 pages.

Barr, John D., "Temporary and Permanent Occlusion of Cerebral Arteries," *Neuroendovascular Surgery*, vol. 11, No. 1, Jan. 2000, pp. 27–38.

Berthelsen, B. et al., "Embolization of Cerebral Arteriovenous Malformations with Bucrylate," *Acta Radiologica*, vol. 31, 1990, pp. 13–21.

Freeny, Patrick C. et al., "Transcatheter Therapy of Genitourinary Abnormalities Using Isobutyl 2–Cyanoacrylate (Bucrylate)," *AJR*, vol. 133, Oct. 1979 pp. 647–656.

Gobin, Dr. Y. Pierre et al., "Treatment of Brain Arteriovenous Malformations by Embolization and Radiosurgery," *J Neurosurg*, vol. 85, 1996, pp. 19–28.

Halbach, Dr. Van V. et al., "Preoperative Balloon Occlusion of Arteriovenous Malformations," *Neurosurgery*, vol. 22, No. 2, 1988, pp. 301–308.

(List continued on next page.)

Primary Examiner—Michael G. Hartley
Assistant Examiner—Frank Choi
(74) Attorney, Agent, or Firm—Gray Cary Ware & Freidenrich LLP; Lisa A. Haile; Kelly K. Reynolds

(57) ABSTRACT

A composition comprising of a monomer component comprised of at least one alkyl cyanoacrylate and at least one inhibitor, and a second component comprised of a resultant aggregate structure formed from an alkyl cyanoacrylate monomer, an alkyl esterified fatty acid and an opacificant agent where said composition forms a resultant aggregate structure when said composition contacts an anionic environment. The compositions are useful for filling, occluding, partially filling or partially occluding an unfilled volume or space in a mass in an anionic environment. The composition are also useful for ablating diseased or undesired tissue by cutting off the blood supply to the tissue.

45 Claims, No Drawings

OTHER PUBLICATIONS

Kerber, Dr. Charles W. and Wong, Wade, "Liquid Acrylic Adhesive Agents in Interventional Neuroradiology," *Neuroendovascular Surgery*, vol. 11, No. 1, Jan. 2000, pp. 85–99.

Lefkowitz, Dr. Michael A. et al., "Balloon–assisted Guglielmi Detachable Coiling of Wide–necked Aneurysms: Part II—Clinical Results," *Neurosurgery*, vol. 45, No. 3, Sep. 1999, pp. 531–538.

Levy, Dr. David I., "Embolization of Wide–necked Anterior Communication Artery Aneurysm: Technical Note," *Neurosurgery*, vol. 41, No. 4, Oct. 1997, pp. 979–982.

Malek, Dr. Adel M. et al., "Balloon–assist Technique for Endovascular Coil Embolization of Geometrically Difficult Intracranial Aneurysms," *Neurosurgery*, vol. 46, No. 6, Jun. 2000, pp. 1397–1407.

Moret, J et al., "The "Remodeling Technique" in the Treatment of Wide Neck Intracranial Aneurysms," *Interventional Neuroradiology*, vol. 3, 1997, pp. 21–35.

Pelz, David M. et al., "Preoperative Embolization of Brain AVMs with Isobutyl–2 Cyanoacrylate," *AJNR*, vol. 9, Aug. 1988, pp. 757–764.

Rao, V.R.K. et al., "Dissolution of Isobutyl 2–Cyanoacrylate on Long–Term Follow–Up," *AJNR*, vol. 10, Jan./Feb. 1989, pp. 135–141.

Spiegel, S. M. et al., "Adjusting the Polymerization Time of Isobutyl–2 Cyanoacrylate," *American Journal of Neuroradiology*, vol. 7, Jan./Feb. 1986, pp. 109–112.

Tseng et al., "Modified Ethoxyethyl Cyanoacrylate for Therapeutic Embolization of Arteriovenous Malformations," *Journal of Biomedical Material Research*, vol. 24, (1990), pp. 65–77.

Vinuela, F.V. et al., "Dominant–Hemisphere Arteriovenous Malformations: Therapeutic Embolization with Isobutyl–2–Cyanoacrylate," *AJNR*, vol. 4, Jul./Aug. 1983, pp. 959–966.

Vinuela, Fernando et al., "Progressive Thrombosis of Brain Arteriovenous Malformations After Embolization with Isobutyl 2–Cyanoacrylate," *AJNR*, vol. 4, Nov./Dec. 1983, pp. 1233–1238.

Vinuela, Fernando et al., "Angiographic Follow–Up of Large Cerebral AVMs Incompletely Embolized with Isobutyl–2–Cyanoacrylate," *AJNR*, vol. 7, Sep./Oct. 1986, pp. 919–925.

* cited by examiner

COMPOSITIONS USEFUL FOR REMODELING BODY SPACES

This application is a continuation-in-part of U.S. Ser. No. 09/241,368, filed Jan. 29, 1999, which is incorporated herein by reference. The present application is also a continuation-in-part of U.S. Ser. No. 09/151,621, filed Sep. 11, 1998, now issued U.S. Pat. No. 6,037,366, which is a conversion of U.S. Provisional Application No. 60/058,510, filed Sep. 11, 1997, both of which are incorporated herein by reference.

FIELD OF THE INVENTION

This invention relates to cyanoacrylate compositions useful as medical devices.

BACKGROUND OF THE INVENTION

Cyanoacrylate tissue adhesives have been in clinical endovascular use since the 1970's. Liquid acrylics are extremely useful as endovascular embolic agents because of their ability to create permanent vascular occlusion. They may, however, be difficult to use technically as they have a variable and sometime unpredictable polymerization time based on the operator selection of an acrylic mix with either iodinated oil or glacial acetic acid. The appropriate choice of polymerization time depends on a number of variables, including the transit time between arterial and venous elements in the embolic target, the target volume, the architecture of the target, for example, a fistula versus nidus, which affects the relative endovascular turbulence, and the method of injection (bolus, full column, or wedge-flow arrest). Typical complications associated with the use of liquid acrylics for embolization occur when there is occlusion of normal arterial branches or acrylic penetration into critical venous outflow channels. Additionally, reflux of acrylic around the delivery catheter tip can result in permanent endovascular catheter adhesion, which may require permanent catheter implantation. Overzealous attempts at withdrawal can produce catheter fracture (and resultant embolization of flow-directable distal catheter segment), vascular damage with resultant dissection/occlusion, or avulsion of the involved vascular pedicle (with resultant subarachnoid hemorrhage).

Alkyl alpha cyanoacrylates are a homologous series of organic molecules which polymerize and can adhere to moist living tissues. The methyl homolog has been used in homeostasis and non-suture closure since 1960, but its histoxicity severely limited its clinical usefulness. The synthesis of longer alkyl chain homologs and the evaluation of these in various animal species have shown that the histoxicity of cyanoacrylates could be diminished without sacrificing their hemostatic and tissue bonding properties. Extensive animal studies have been completed using n-butyl and isobutyl homologs, and preliminary human trials have been undertaken.

Polymerization speed is another function of chain length. It has been reported that homologs with six or more carbon atoms on the alkyl chain polymerize almost immediately upon contact with moist tissues. The n-butyl and isobutyl monomers require from four to 15 seconds, while the methyl homolog remains as a monomer for 30 to 55 seconds. The ability to wet and spread easily over the surface of an anticoagulated blood film is common to homologs with alkyl chains containing four or more carbon atoms. The ethyl and propyl derivatives wet and spread poorly, and the methyl not at all.

Since the advent of NBCA (n-butyl-2-cyanoacrylate), there has been very little advancement in the science of "superglue" embolization of vascular structures, primarily arteriovenous malformations (AVMs). Certain properties of superglue are advantageous for embolization, such as adhesion, the ability transform from a liquid or solid state and rapid polymerization. However, these properties can be detrimental when present to an excessive degree, in particular, adhesion which can result in permanent catheter fixation. Rapid polymerization allows the material to set in flowing blood without passing through small channels into venous structures. However, rapid polymerization may also release amounts of heat that can cause damage to the surrounding tissue, for example, brain tissue.

Hydrophilic catheter coatings have been developed in the hope of reducing the risk of inadvertent endovascular catheter fixation during embolization due to reduced bond strength between the hydrophilicly coated catheter and the adhesive. However, micro catheter cyanoacrylate adhesion remains a problem during intravascular embolization. Inadvertent gluing of the catheter tip onto the artery is a well recognized and distressing complication. Vessel rupture or occlusive embolization of a detached catheter tip may occur if excessive force is used to attempt to retrieve the catheter. Fortunately, permanent intra vascular catheter fixation is usually well tolerated, nonetheless this remains a highly undesirable event. An in vitro study has shown that recently available hydrophilic micro catheter coatings decrease catheter adhesion of both pure normal butyl cyanoacrylate and mixtures of normal butyl cyanoacrylate and ethiodized oil. Although hydrophilicly coated catheters have the potential of decreasing the occurrence of inadvertent endovascular catheter fixation, the level of operator proficiency and experience, and perhaps most importantly, the actual adhesive composition that is used stills play a major role in these events.

There exists a continuing unmet need for a composition that has the correct amount of cohesiveness, produces a robust rubbery casting, is tolerated by the body, can trigger the appropriate amount of tissue inflammation response and is radiopaque.

It has now been surprisingly found that such a composition exists that has the requisite combination of properties in cohesion, stability, body tolerance, low catheter adhesion and radiopacity.

SUMMARY OF THE INVENTION

A composition comprising of a monomer component comprised of at least one alkyl cyanoacrylate and at least one inhibitor, and a second component comprised of a resultant aggregate structure formed from an alkyl cyanoacrylate monomer, an alkyl esterified fatty acid and an opacificant agent where said composition forms a resultant aggregate structure when said composition contacts an anionic environment. The compositions are useful for filling, occluding, partially filling or partially occluding an unfilled volume or space in a mass in an anionic environment. The composition are also useful for ablating diseased or undesired tissue by cutting off the blood supply to the tissue.

BRIEF DESCRIPTION OF THE DRAWINGS

No drawings are included.

DETAILED DESCRIPTION OF THE INVENTION

The present invention provides a composition comprising of a monomer component comprised of at least one alkyl cyanoacrylate, at least one inhibitor and a second component that functions as a opacificant agent and polymerization retardant. The composition is useful for filling, occluding, partially filling or partially occluding an unfilled volume or space in a mass ("a space"). In particular, the composition is useful for filling an existing space, e.g., the lumen of a blood vessel, or the sac of an aneurysm, a space created by a transiently placed external device, e.g., a catheter or like device, a space created by a procedure, e.g., an excision or like procedure or implantation of an object, e.g., a stent or like device, or a space created by the composition; the composition is also useful for adhering tissue to tissue, or adhering tissue to a device. The composition has the property of polymerizing when it comes in contact with an anionic environment, or when it is deployed in situ in an existing space, e.g., the lumen of a blood vessel, or the sac of an aneurysm, a space created by a transiently placed external device, e.g., a catheter or like device, a space created by a procedure, e.g., an excision or like procedure or implantation of an object, e.g., a stent or like device, or a space created by the composition;

Another aspect of the present embodiment is where the second component is comprised of a halogenated oil. Preferred are iodinated and brominated oils, such as Ethiodol, Lipiodol and Pantopaque. Most preferred is Ethiodol.

One embodiment of the present invention is where the second component is Ethiodol.

Another aspect of the present embodiment is where the second component is comprised of a resultant aggregate structure, i.e., an oligomer or polymer, formed from a composition of alkyl cyanoacrylate monomer, an alkyl esterified fatty acid and an opacificant agent.

Another aspect of the present embodiment is where the monomer component is comprised of one alkyl cyanoacrylate monomers, and at least one inhibitor. A preferred aspect is where the monomer component is comprised of 2-hexyl cyanoacrylate and one inhibitor. An especially preferred aspect is where the monomer component is comprised of 2-hexyl cyanoacrylate, and three inhibitors, most especially preferred is the aspect where the inhibitors are hydroquinone, p-methoxyphenol and phosphoric acid. An especially preferred embodiment of the present invention is a composition comprised of the present monomer component, and a second component comprising of a resultant aggregate structure, i.e., an oligomer or polymer, formed from 2-hexyl cyanoacrylate monomer, an alkyl esterified fatty acid and an opacificant agent, most especially preferred is where the alkyl esterified fatty acid is ethyl myristate and the opacificant agent is gold.

Another aspect of the present embodiment is where the monomer component is comprised of two or more different alkyl cyanoacrylate monomers, and at least one inhibitor. A preferred aspect is where the monomer component is comprised of methyl cyanoacrylate, n-hexyl cyanoacrylate and at least one inhibitor. An especially referred aspect is where the monomer component is comprised of methyl cyanoacrylate, n-hexyl cyanoacrylate and at least three inhibitors, a most especially preferred aspect is where the inhibitors are hydroquinone, p-methoxyphenol and acetic acid. A particularly preferred embodiment of the present invention is the composition comprised of the present monomer component, and a second component comprising of the resultant aggregate structure, i.e., an oligomer or polymer, formed from n-hexyl cyanoacrylate monomer, an alkyl esterified fatty acid and an opacificant agent, most preferred is where the alkyl esterified fatty acid is ethyl myristate and the opacificant agent is gold.

Another embodiment of the present invention is a method for purifying alkyl cyanoacrylate monomer to its crystalline form. In particular, a method of purifying an alkyl cyanoacrylate to about 95% purity or better, preferred is to about 97% purity or better, most preferred is to about 98% purity or better, and most especially preferred is to about 99% purity or better.

Another embodiment of the present invention is a substantially pure alkyl cyanoacrylate monomer. In particular, methyl cyanoacrylate, n-butyl cyanoacrylate, isobutyl cyanoacrylate, n-hexyl cyanoacrylate, 2-hexyl cyanoacrylate and 2-octyl cyanoacrylate, purified to about 95% purity or better, preferred is to about 97% purity or better, most preferred is to about 98% purity or better, and most especially preferred is to about 99% purity or better. A particularly advantageous aspect of the present invention is where the alkyl cyanoacrylate monomer is isolated in its crystalline form.

It is known to those of ordinary skill in the art that the predictability of polymerization properties of alkyl cyanoacrylate monomers is related to the purity of the monomer that are used. These polymerization properties, include but are not limited to rate of polymerization, and stability of the monomer during storage. Another advantage of substantially pure alkyl cyanoacrylates is that compositions incorporating substantially pure alkyl cyanoacrylates require smaller amounts of additives, e.g., inhibitors, stabilizers and the like, to obtain a desired result that would otherwise have require greater amounts of the same additive. An immediate benefit of this advantage is in cost savings from being able to use less material. Another benefit, is that the composition will quantitatively have lower amounts of additives. This is a desirable outcome for any composition that is subject to regulatory approval by the U.S. Food and Drug Administration, or like agency, prior to marketing. The current embodiment provides alkyl cyanoacrylate monomers whose rates of polymerization can be predicted, and where the un-reacted monomer ("pre-polymer") compositions are more stable. The properties provide beneficial advantages for the use of the compositions of the present invention because by being able to predict the polymerization characteristics of a monomer, one of ordinary skill in the art can select the monomer with the appropriate polymerization properties for a desired use, or to formulate monomer compositions having desired polymerization properties. Prior to the present invention, alkyl cyanoacrylates have not been available in substantially pure form because they are difficult to purify using conventional chemical methodology. Moreover, most of these methodologies involve conditions that cause the alkyl cyanoacrylate to degrade or to spontaneously polymerize. Therefore before the present invention, the benefits of substantially pure alkyl cyanoacrylate monomers were not available.

Another embodiment of the present invention provides a method for filling, occluding, partially filling or partially occluding an unfilled volume or space in a mass. The types of unfilled volumes or spaces within the scope of the present invention includes, but are not limited to the following instances.

For example, one aspect of the present embodiment is a method of filling, occluding, partially filling or partially occluding an existing space, such as, a lumen of a passageway in the body, e.g., a blood vessel, a duct, an aneurysm, or a fistula. Examples of the types treatments covered by this method of use, include but are not limited to the following. The present invention is useful as a method of treating arteriovenous malformations (AVM) where the blood vessel (s) that feed the AVM are occluded thereby cutting off the blood supply to the AVM. The present invention is useful as a method to ablate diseased or undesired tissue by cutting off the tissue's blood supply. In particular, the present invention is useful as a method of treating a tumor having a discrete blood supply, where the blood vessel(s) that feed the tumor are occluded thereby cutting off the blood supply to the tumor resulting in diminished growth or death of the tumor. The present invention is useful as a method of preventing or mitigating the development of an aneurysm by creating a partial occlusion at a location in the blood vessel selected to modify the fluid dynamics within the vessel to mitigate the formation or development of an aneurysm. The present invention is useful as a non-surgical method of treating symptomatic uterine leiomyomas by embolizing/occluding the uterine artery. This method has been reported using a non alkyl cyanoacrylate composition in *Journal of Vascular and Intervention Radiology,* 10:891–894, July–August 1999. The present invention is useful as a method of sterilizing a female mammal by occluding the fallopian tubes thereby preventing the passage of the eggs from the ovaries to the uterus. The use of an occluding agent to sterilize a female mammal is disclosed in U.S. Pat. No. 5,989,580 "Method of Sterilizing Female Mammals," herein incorporated by reference. The methods disclosed in this patent can be advantageously applied using the compositions of the present invention, and are within the scope of the present invention. The methods disclosed in this patent can be advantageously applied using the compositions of the present invention, and are within the scope of the present invention. The present invention is useful for obliterating the left atrial appendage. The left atrial appendage is derived from the left wall of the primary atrium. It has been observed that patients with atrial fibrillation have a predilection for thrombus to form in the in the left atrial appendage. A review of this condition and the current status of treatment is disclosed in the article, "Left Atrial Appendage: structure, function, and role in thromboembolism" N. M. Al-Saady, et. al. The present invention provides an advantageous method of obliterating the left atrial appendage.

Another aspect of the present embodiment is a method of filling, occluding, partially filling or partially occluding a space created by a transiently placed external device, such as, a catheter balloon. a space created by a transiently placed external device, e.g., a catheter or like device. Examples of the types of treatments covered by this method of use include, but are not limited to the following. The present invention is useful as a method of treating an aneurysm by filling the space within the aneurysm with a composition of the present invention, where the composition polymerizes in the space within the aneurysm, thereby preventing the rupture of the aneurysm. This treatment can be effected using the present invention with any number of catheters, catheter coils, catheter wires or catheter balloons commercially available. Examples of such devices are commercially available from sources. For instance, Micro Therapeutics, Inc., 2 Goodyear, Irvine, Calif. 92618, markets a line of medical devices, such as, the Rebar™ Micro Catheter, Equinox™ Occlusion Balloon System and SilverSpeed™ guidewires. Similarly, U.S. Pat. No. 5,882,334 "Balloon/ delivery Catheter Assembly with Adjustable Balloon Positioning," assigned to Target Therapeutics, Inc., and incorporated herein by reference, is directed to a catheter assembly for delivering compositions, such as, those of the present invention.

Another aspect of the present embodiment is a method of filling, occluding, partially filling or partially occluding a space created or resulting from a procedure, such as with the excision of tissue, or insufflation. Examples of the types of treatments covered by this method of use include, but are not limited to the following. The present invention is useful as a method of treating or mitigating capillary oozing.

Another aspect of the present embodiment is a method of filling, occluding, partially filling or partially occluding a space created by the placement or implantation of an object, such as, a medical device. Examples of the types of uses covered by this method of use include, but are not limited to the following. The resent invention is useful as a method of restoring the normal fluid dynamics at the peripheral edges of a vascular stent by filling the dead spaces between the stent and the lumen wall created by the implantation of the stent.

Another aspect of the present embodiment is a method of filling, occluding, partially filling or partially occluding a space created by the composition itself, such as, where the composition is used as a bulking agent. Examples of the types of uses covered by this method of use include, but are not limited to the following. For example, a method of recreating the normal contours to skin following an adverse event, such as, physical trauma.

Another embodiment of the present invention provides a method of affixing therapeutics, chemotherapeutics, radiation delivery devices, gene therapy compositions to a desired location where the active agents can be advantageously maintained in proximity to the desired location. The active agent is then release gradually as the resultant aggregate structure from the composition of the present invention is biodegraded. Alternatively, the composition of the present invention can be modified to allow for a specific rate of delivery. This use is particularly beneficial in the treatment of tumors that are ideally treated by localized dosages of chemotherapy or radiation. An advantage of this method is that the patient would not be subjected to as large of a dose of the therapeutic or radiation as would be necessary, if the therapeutic or radiation was administered on a systemic basis. Another advantageous use the present invention is for the delivery of DNA compositions used in gene therapy. A long standing problem in the gene therapy arts has been the inability of practitioners to deliver the DNA therapeutic to the locales in the body most ideally suited for the treatment. The present invention provides a method of affixing the DNA composition at a desired site, where the active agent is then slowly released over a period time as the composition of the present invention biodegrades. Alternatively, a composition of the present invention can be modified to release the active agent in a controlled delivery manner.

Another embodiment of the present invention provides a method of utilizing magnetically controlled particles embedded in a composition of the present invention to deploy the composition to a desired location, "Magnetic Probe for the Stereotaxic Thrombosis of Intracranial Aneurysms," Alksne, J. F., et. al, *Journal of Neurology,* Neurosurgery and Psychiatry, 1967 April, 30(2):159–62; "Magnetically Controlled Focal Intravascular Thrombosis in Dogs" Alksne, J. F., et. al, *Journal of Neurosurgery,* 1966 November, 25(5): 516–25; "Thrombosis of Intracranial Aneurysms—An experimental approach utilizing magnetically controlled iron particles" Alksne, J. F., et. al, *Radiology* 1966 February 86(2):342–3.

Another embodiment of the present invention provides a method of adhering, joining, connecting or affixing a first section of tissue to a second section of tissue. Examples of the types of uses covered by this method of use include, but are not limited to the following. The present invention is useful as a method of adhering, joining, or connecting two blood vessels, e.g., anastomoses, where blood vessels are quickly and efficiently adhered, joined or connected, under surgical conditions without the use of sutures or staples. The present invention is useful as a method of treating primary wounds or wounds that require immediate intervention, such as, trauma wounds, where the compositions of the present invention are used to temporarily close the wound to minimize the lost of fluids due to evaporation, and to mitigate infection.

Another embodiment of the present invention provides a method of adhering, joining, connecting, or affixing tissue to a non-tissue surface, such as a medical device. Examples of the types of uses covered by this method of use include, but are not limited to the following. The present invention is useful as a method of implanting or securing venous valves, replacement heart valves, or stents at their desired location.

The aforementioned uses are possible because the compositions of the present invention remain in a controllable state for a period of time in excess of 1 second after being deployed from an administration device. This property allows the practitioner to incremental maneuver the deployment of the composition to its most ideal location, even though the composition had been partially deployed distal to the deployment device.

For instance, the compositions of the present invention have adequate cohesion to maintain its continuity once it is outside of the deployment device. Without adequate cohesion the composition would break into smaller aggregates dispersing into the blood flow.

For instance, the compositions of the present invention have appropriate adhesion properties so that when desired a deployed composition adheres to the immediate location where it is deployed so that the resultant aggregate of the monomer is placed where it is desired.

The compositions of the present invention have polymerization rate, such that, the practitioner can effect the desired amount of penetration of the composition into a particular type of space. A composition that polymerizes too quickly would hinder penetration, conversely a composition that polymerizes too slowly would make it difficult to precisely place the polymerized composition resultant aggregate of the monomer.

Another embodiment of the present invention provides a method for selectively creating an embolic blockage in the lumen of a blood vessel, duct, fistula or other like body passageways.

Another embodiment of the present invention provides a method of treating arteriovenous malformation (AVM).

Definitions

As used herein the terms "adhesion" or "adhesive" means the characteristic or tendency of a material to be attracted to the surface of a second material. Adhesion occurs as the result of interactions between two materials. Depending on the characteristics of the second material relative to the first material, adhesion may or may not occur. For a single material, e.g., the composition of the present invention, the presence of adhesion is demonstrated by a material sticking to the wall of a lumen of blood vessel, i.e., there is adhesion between the material and the lumen wall. Conversely, the absence of adhesion is demonstrated for the same material where a micro-catheter tip used to deposit the material can be removed from the material, i.e., there is little adhesion between the material and micro-catheter tip.

As used herein the term "alkyl" refers to a carbon chain of one to sixteen carbon atoms, where the carbon atoms can be linear or branched.

As used herein the term "anionic environment" or "anionic environment" refers to an environment that is non-ionic. This an environment that is devoid of charged ions, or where the charged ions are complexed with other molecules which effectively neutralize their charge. For example, a solution of water and a sugar, such as, dextrose, and blood, is an anionic environment.

As used herein the term "lower-alkyl" refers to a carbon chain of one to eight carbon atoms, where the carbon atoms can be linear or branched. Examples of lower-alkyl moieties include but are not limited to methyl, ethyl, n-butyl, isobutyl, pentyl, n-hexyl, 2-hexyl, n-heptyl, 2-heptyl, n-octyl and 2-octyl.

As used herein the term "branched alkyl" refers to a carbon chain of one to sixteen carbon atoms where the carbon chain contains at least one secondary or tertiary substituted carbon atom.

As used herein the term "branched lower-alkyl" refers to a carbon chain of one to eight carbon atoms where the carbon chain contains at least one secondary or tertiary substituted carbon atom, for example, 2-hexyl, isobutyl, 2-heptyl and 2-octyl.

As used herein the term "cohesion" or "cohesive" means the characteristic or tendency of a material to stick together to itself. For example, this characteristic is demonstrated by a material or composition remaining intact as a single mass when introduced into a stationary fluid, or a fluid stream in motion, such as, blood. Lack of cohesive integrity results in the composition breaking up into multiple smaller subunits.

As used herein the term "embolic agent" refers to a non-naturally occurring composition introduced into a body cavity or the lumen of a blood vessel, duct, fistula or other like body passageways for the purpose of forming an embolic block.

As used herein the term "embolic block" or "embolic blockage" or occlusion refers to the end result from the administration of a composition useful as an embolic agent. The resulting embolic block mechanically blocks, totally or partially, the lumen of a blood vessel, duct, fistula or other like body passageways; or in a like manner forms an occlusion within a cavity, such as an aneurysm.

As used herein the term "alkyl cyanoacrylate monomer" refers to the chemical entity of the general structure $H_2C=C(CN)-C(O)O-R$, where R is an alkyl moiety of one to sixteen carbon atoms, linear or branched, saturated or unsaturated, having the physical characteristic of being able to form the corresponding alkyl cyanoacrylate.

As used herein the term "alkyl cyanoacrylate polymer" means an oligomer or polymer resulting from the polymerization of a alkyl cyanoacrylate monomer.

As used herein the term "alkyl esterified fatty acid" means a fatty acid derivatized to form an ester functional group with a alkyl moiety, such as ethyl myristate. These compounds are formed with an alkyl moiety, such as methyl, ethyl, propyl, butyl, pentyl, hexyl, heptyl, and octyl; and carboxylic acids with alkyl side chains ranging from 1 carbon, i.e., acetic acid, through to and including 17 carbons atoms in length, such as, proprionic, butyric, isobutyric, valeric, isovaleric, pivalic, lauric, myristic, palmitic and stearic acids.

As used herein the term "opacificant agent" is compound or composition which selectively absorbs or deflects radiation making the material visible under x-ray, or any like imaging technique. Typically such agents include, iodinated oils, and brominated oils, as well as commercially available compositions, such as Pantopaque, Lipiodol and Ethiodol. These commercially available compositions acts as opacificant agents, and also dilute the amount of liquid monomer thereby slowing the rate of polymerization. In addition certain metals, such as, gold, platinum, tantalum, titanium, tungsten and barium sulfate and the like, have properties enabling them to act as opacificant agents.

As used herein the term "polymerization" refers to the chemical process where identical monomer units react chemically to form larger aggregates of said monomeric units as oligomers or polymers.

As used herein the term "polymerization retardant" means an agent that can stop or slow down the rate of polymerization. Examples of such agents are pure phosphoric acid, and 85% phosphoric acid. Certain opacificant agents, such as Pantopaque, Lipiodol and Ethiodol can also function as a polymerization retardant by diluting the amount of liquid monomer and hence slowing polymerization rate.

As used herein the term "a space" refers to an unfilled volume or cavity in a mass. Examples of such spaces, include but are not limited by the following, an existing space within a mass, such as, the lumen of a blood vessel, the sac of an aneurysm; a space created by a transiently placed external device, such as, a catheter or like device; a space created by a procedure, such as, an excision or like procedure; a space created by implantation of an object, such as, a stent or like device; or a space created by the composition.

As used herein the term "stability" refers to the ability of a monomer component to resist degradation or polymerization after preparation but prior to use.

As used herein the term "inhibitor agent" refers to an agent which stabilizes a monomer composition by inhibiting polymerization. Within the context of the current invention, this term refers to agents that stabilize and inhibit polymerization by various mechanisms. By altering the amounts of one or more inhibitor agents, the rate of polymerization can be controlled. Inhibitor agents have different modes of activity, for example, hydroquinone acts primarily to inhibit high energy free radicals; p-methoxyphenol acts primarily to inhibit low energy free radicals; and phosphoric acid influences the rate of anionic polymerization.

As use herein the term "Neuracryl M" refers to the composition comprising of a monomer component ("M1") comprised of 2-hexyl cyanoacrylate, hydroquinone, p-methoxyphenol and phosphoric acid, and a second component ("M2") comprising of a resultant aggregate structure formed from 2-hexyl cyanoacrylate monomer, ethyl myristate and gold. As noted above, the term "M1" refers to the monomer component of Neuracryl M, and the term "M2" refers to the second component of Neuracryl M.

As used herein the term "Neuracryl A" refers to the composition comprising of a monomer component ("A1") comprised of n-hexyl cyanoacrylate, methyl cyanoacrylate, hydroquinone, p-methoxyphenol and acetic acid, and a second component ("A2") comprising of a resultant aggregate structure formed from n-hexyl cyanoacrylate monomer, ethyl myristate and gold. The term "A1" refers to the monomer component of Neuracryl A, and the term "A2" refers to the second component of Neuracryl A.

As used herein the term "deployment device" refers a device used to deploy compositions, such as, those of the present invention. Examples of such devices, include but are not limited to the following. Micro Therapeutics, Inc., 2 Goodyear, Irvine, Calif. 92618, markets medical devices, such as, the Rebar™ Micro Catheter, Equinox™ Occlusion Balloon System and SilverSpeed™ guidewires, that are used in conjunction for treating conditions such as those within the present invention. The devices disclosed in U.S. Pat. No. 5,882,334 "Balloon/delivery Catheter Assembly with Adjustable Balloon Positioning," incorporated herein by reference, is directed to a catheter assembly for delivering compositions.

Nomenclature

The compound 2-hexyl cyanoacetate is depicted as follows, and also as Formula 3 in Schemes A and B.

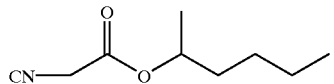

The compound 2-hexyl cyanoacrylate is depicted as follows, and also as Formula 5 in Scheme B.

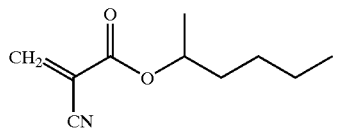

The present invention is a composition formed from alkyl cyanoacrylate monomeric units, such as, methyl, n-butyl, isobutyl, n-hexyl and 2-hexyl cyanoacrylate with at least one inhibitor agent, such as hydroquinone, p-methoxyphenol and phosphoric acid. The composition forms into its resultant aggregate structure, i.e., an oligomer or polymer, when it comes in contact with an anionic environment, such as, blood or tissue. The resultant aggregate composition has characteristics which makes it particularly well suited as an embolic agent.

The composition of the present invention possess the following properties, which are desirable in an embolization agent.

1) The composition can be prepared and maintained as a monomeric component and second component until needed.
2) The composition has the ability to reliably and predictably change from a liquid state to a solid state, which is essential for its introduction and controlled placement into the lumen of vessel, duct, fistula or other like body passageways.
3) The composition has low viscosity, which is essential for its administration by syringes and micro-catheters or other like devices.
4) The composition has cohesive characteristics such that when the composition in administered into an anionic fluid environment, such as blood, the composition forms a single aggregate structure.
5) The composition has adhesive characteristic such that it attaches to the lumen of vessel, duct, fistula or other like body passageways, but not to the degree where the device depositing the composition will become fixed to it before the practitioner can remove it.
6) The composition causes mild tissue inflammation, sufficient to cause scarring, but not so severe to cause the formation of pus. Scar formation is necessary to maintain the functionality of the embolic block after the composition has biodegraded, or otherwise eliminated from the lumen.
7) The composition is sufficiently stable to biodegradation to allow for scarring to occur.
8) The composition is radiopaque. Although not necessary for its function as an embolic agent, radiopacity allows the embolic block to be observed with x-ray or other such imaging techniques.

9) The rate of heat released during polymerization of the composition is low enough such that the heat does not adversely effect surrounding tissues that may be heat sensitive, such as brain tissue.

10) The composition and its biodegradation products are sufficiently non-histotoxic and non-cytotoxic so that its presence is well tolerated in the body.

The composition of the present invention is used by combining the monomer component and second component. Upon mixing of the components, the invention is administered into the lumen of a blood vessel, duct, fistula or other like body passageways. The characteristics of the present invention permit its accurate placement in the lumen. Contact with an anionic environment, such as blood, or tissue causes the composition to polymerize. The size of the resultant embolic block formed is determined by the amount of composition administered.

The characteristics of the composition of the invention can be modified for a specific purpose or environment for which the embolic agent is intended to be utilized. For example, changes in the length and isomeric configuration of the alkyl side chains can alter the brittleness of the resultant aggregate of cyanoacrylate monomers. Alkyl chains that result in the formation of smaller aggregates tend to be less brittle, while larger aggregates tend to be less flexible. In addition, by combining monomers with different alkyl side chains the characteristics of the resultant polymer can be modified to what is optimal for a desired application.

Cyanoacrylates generate heat as they change from monomeric to polymeric form. The amount and rate of heat released, if excessive, can have a detrimental effect on the living tissue proximate to the vessel. Control of the amount and rate at which heat is release during polymerization is critical to the utility of composition.

Preparation of the Monomer Component

The monomer component of the present invention is prepared by forming the desired precursor ester from the corresponding alkyl alcohol and cyanoacetic acid resulting in the desired alkyl cyanoacetate as depicted in Scheme A. The starting materials for this reaction are commercially available, for example from Aldrich Chemical Company, Sigma Chemical Company or Fluka Chemical Company, or can be prepared following procedures known to those of ordinary skill in the art.

Scheme A

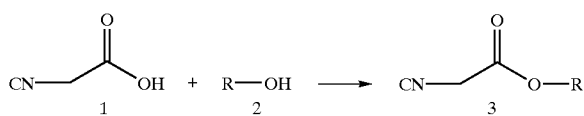

The compound of Formula 2 can be any alkyl alcohol, where R is from one to sixteen carbons, including but not limited to alcohols based on alkyl groups, such as, methyl, ethyl, propyl, butyl, pentyl, hexyl, heptyl, heptyl, octyl, nonyl, deca, undeca, dodeca, trideca, tetradeca, pentadeca and hexadeca, where the preceding moieties are linear (e.g., n-propyl, n-butyl, n-pentyl) or variously branched, such as sec-butyl, iso-butyl, tert-butyl, iso-propyl, 2-butyl, 2-pentyl, 2-hexyl, 2-heptyl, 2-octyl and the like. Particularly advantageous alcohols are those disclosed in U.S. Pat. No. 3,728,375 entitled "Cyanoacrylate Adhesive Compositions", which is hereby incorporated by reference. Especially preferred are methyl, n-butyl, iso-butyl, n-hexyl and 2-hexyl alcohols.

About 1 molar equivalents of the compounds of Formula 1 and Formula 2 are combined in a solvent like toluene at about 100 ml/molar equivalents. To this mixture is added a catalytic amount (about $1.0 \times 10^{-4}$ molar equivalents) of p-toluene sulfonic acid. The mixture is stirred and heated to reflux. The preparation ideally yields the desired alkyl cyanoacetate at a purity level of about 95%. The experimental conditions can be readily modified by one of ordinary skill in the art without deviating from the present invention. Aspects such as, solvent selection, reaction time, temperature and choice of reagents are well within the skill of one of ordinary skill in the art. If necessary, the material can be further purified using multiple distillations and purification techniques and procedures known to those of ordinary skill in the art, such as water extraction, vacuum distillation, column chromatography, and the like.

Preparation of Alkyl Cyanoacrylate

The desired alkyl cyanoacrylate monomer component of the present invention is synthesized from the alkyl cyanoacetate by reacting the it in a Knöevengel type reaction as depicted in Scheme B.

Scheme B

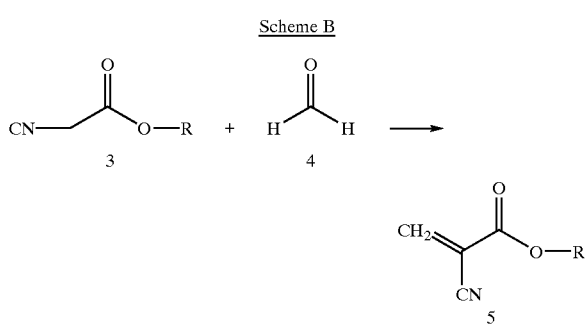

About 1 molar equivalents of formaldehyde (Formula 4), which is prepared from paraformaldehyde, and piperidine (at about 0.33 ml/molar equivalents) are combined in a solvent, such as methanol (at about 166 ml/molar equivalents). To this mixture is added about 1 molar equivalents of previously prepared alkyl cyanoacetate (Formula 3) in a dropwise manner. The reaction mixture is refluxed with stirring yielding the desired alkyl cyanoacrylate polymer (Formula 5). The reaction mixture is further processed with about 0.2 to 0.7 molar equivalents, preferably about 0.2 to 0.6 molar equivalents of phosphorous pentoxide yielding the desired alkyl cyanoacrylate. Care must be taken during purification steps to prevent the compound of Formula 5 from polymerizing. To this end the system is treated with trace amounts of sulfur dioxide, and receiver flasks are treated with hydroquinone and 85% phosphoric acid. After initial purification, the desired alkyl cyanoacrylate is further purified using multiple distillations, or other purification techniques known to those of ordinary skill in the art, such as, vacuum distillation, spinning band column, and the like.

Purification of Composition by Zone Freeze/Melting

The alkyl cyanoacrylate monomer compositions of the present invention can be purified using the zone melting technique to a point where under the correct conditions it is possible to form pure crystals of the alkyl cyanoacrylate monomers, such as, methyl cyanoacrylate, -butyl cyanoacrylate, iso-butyl cyanoacrylate, n-hexyl cyanoacrylate, and 2-hexyl cyanoacrylate.

The composition is placed in a container fitted with an exchange apparatus, which will permit the differential removal of liquid impurities from the composition. The pressure of the container with the composition is reduced to about 1.5 to 0.5 Torr, preferably about 1 Torr, at the same time the temperature of the composition is reduced to about −28 to −8° C., preferably about −23 to −13° C., most preferably about −17.5 to −18.5° C. The composition is allowed to equilibrate at this temperature for a period of about 12 to 36 hours, preferably about 24 hours. After the equilibration period, the alkyl cyanoacrylate is crystallized out of solution by gently agitating the container, such as by tapping the side of the container, or gently shaking the container. If the crystallization does not begin, the process is repeated every 15 minutes for 1 hour. If after an hour the alkyl cyanoacrylate still does not crystallize, a small piece of dry ice is placed against the outside of the container for about 30 seconds. Once the alkyl cyanoacrylate monomer begins to crystallize, the temperature of the container is increased by about 6° C., preferably about 4° C., most preferably about 2° C. The crystallization process is allowed to sit undisturbed for about 24 to 72 hours, preferably about 48 hours. At the end of the crystallization period, the container is inverted so that the uncrystallized liquid in the container is drained into the reserve reservoir. The container is allowed to drain for about 30 minute or whatever time is required for the draining of the liquid to be completed. Once the draining is finished the valve between the container with the alkyl cyanoacrylate crystals and the reserve reservoir with the uncrystallized liquid is closed, separating the crystals from the liquid. The liquid is removed from the reserve reservoir and analyzed for the type and amount of impurities. Air is re-introduced into the container with the crystals. The container is also allowed to equilibrate to ambient room temperature, at which time the crystals melts. The melted crystals are analyzed for purity. The purified crystals of the alkyl cyanoacrylate monomer should be reformed into the stable composition of the present invention to prevent the monomer from polymerizing.

If the desired, the process is repeated in order to obtain the alkyl cyanoacrylate monomer at a desired purity. Generally, the process is repeated at least once to gain desired purity. Following purification, the crystalline alkyl cyanoacrylate should be re-formulated into the stable composition of the present invention to prevent the monomer from polymerizing.

Formulation

The monomer component of the present invention comprises of at least one alkyl cyanoacrylate and at least one inhibitor agent. Typical inhibitors appropriate for cyanoacrylates are, for example, hydroquinone, p-methoxyphenol, pure phosphoric acid, and alkyl carboxylic acids, where the alkyl moiety ranges from 1 carbon, e.g., acetic acid, through to 15 and 17 carbons atoms in length, i.e., palmitic and stearic acids, respectively; and phosphoric acid at varying percentage solutions. Preferably hydroquinone, p-methoxyphenol, acetic acid and phosphoric acid are used, individually or in combination.

Different inhibitors have different physical characteristics and thereby functions to alter the final properties of the composition. For example, hydroquinone is primarily an inhibitor for high energy free radicals; p-methoxyphenol is primarily an inhibitor for low energy free radicals; and phosphoric acid acts to control or inhibit anionic polymerization and the rate of such polymerization.

The quantity of inhibitors used is measured in terms of parts per million of alkyl cyanoacrylate. For example, for 2-hexyl cyanoacrylate, hydroquinone is in the range of about 50 to 150 parts per million (PPM), p-methoxyphenol in the range of about 50 to 150 PPM, and phosphoric acid in the range of about 125 to 375 PPM, more preferred is hydroquinone in the range of about 75 to 125 PPM, p-methoxyphenol in the range of about 75 to 125 PPM, and phosphoric acid in the range of about 187.5 to 312.5 PPM, and most preferred is hydroquinone in the range of about 95 to 105 PPM, p-methoxyphenol in the range of about 95 to 105 PPM, and phosphoric acid in the range of about 200 to 300 PPM. Similarly, for a monomer component comprising of 90% n-hexyl cyanoacrylate and 10% methyl cyanoacrylate, hydroquinone is in the range of about 50 to 150 parts per million (PPM), p-methoxyphenol is in the range of about 50 to 150 PPM, and acetic acid is in the range of about 50 to 500 PPM, more preferred is hydroquinone in the range of about 75 to 125 PPM, p-methoxyphenol in the range of about 75 to 125 PPM and acetic acid in the range of about 100 to 300 PPM, and most preferred is hydroquinone in the range of about 95 to 105 PPM, p-methoxyphenol in the range of about 95 to 105 PPM, and acetic acid in the range of about 150 to 250 PPM.

The second component functions as an opacificant agent and a polymerization retardant. To this end, the second component can be an iodinated oil, such as Ethiodol, or a brominated oil. Typically the iodinated oil is mixed as some percent of the total volume of the final composition. The percentage solution of iodinated oil used will influence the polymerization rate and opacity of the composition. Generally advantageous ranges are from about 17% to 66%, preferably about 33%.

Alternatively, the second component can be a composition comprising, a opacificant material, such as gold, platinum, tantalum, titanium, tungsten and barium sulfate and the like; an alkyl cyanoacrylate polymer material, and an esterified fatty acid, where the fatty acids have 3 carbon atoms, for example, alkyl butyrate to 17 carbons, for example, alkyl stearate, preferred are, alkyl laurate, alkyl myristate, alkyl palmatate, and alkyl stearate, most preferred is alkyl myristate, and most especially preferred is ethyl myristate. The opacificant material is used in a fine powder form, typically, with individual particles sized no larger than about 7 microns in diameter, preferably about 5 microns, most preferred about 2 microns and most especially preferred is 1 micron or smaller.

The amount of opacificant material used relative to alkyl cyanoacrylate polymer will vary according to the specific materials. Factors that influence the determination of the ratio include the amount and size of the particles that are being coated by the alkyl cyanoacrylate polymer. For example, for 2-hexyl cyanoacrylate and gold, 2 g of 2-hexyl cyanoacrylate is used per 100 g of powdered gold (particle size of about 5±2 microns) being coated. For example, for n-hexyl cyanoacrylate and gold, 2 mg of n-hexyl cyanoacrylate is used per 1 gm of gold at a particle size of about 2 to $10\mu$, preferably about 0.1 to $1.0\mu$, most preferably about 1 Å. The amounts vary accordingly with the opacificant material being coated by the alkyl cyanoacrylate. The alkyl cyanoacrylate and opacificant material are mechanically mixed by processing the alkyl cyanoacrylate into small particulate masses, and mixing with the finely powdered opacificant material. The alkyl cyanoacrylate polymer coated material is then stored in an esterified fatty acid, which serves as a medium where the alkyl cyanoacrylate polymer coated material is maintained prior to use, and as a medium, which when contacted with the monomer component will not interfere with the polymerization of the composition. The unsealed storage containers, preferably appropriately sterilized bottles and caps or the like, with the cyanoacrylate polymer suspension is then treated with ethylene oxide, or alternatively ketene. This treatment should occur no later than about 48 hours after completion of the coating process, preferably within 24 hours. The treatment process provides sterilization and stabilization of the alkyl cyanoacrylate polymer coated material and follows standard procedures for ethylene oxide use, i.e., positioning the containers so that they are amply exposed to the gas for a sufficient period of time.

Polymer M and Polymer A

The characteristics of the composition of the invention can be modified for a specific application or environment in which the composition is intended to be utilized. For example, changes in the length and isomeric configuration of the alkyl side chains can alter the brittleness of a polymer formed from a cyanoacrylate monomer. Alkyl chains that result in the formation of smaller aggregates tend to be less brittle, while larger aggregates tend to be less flexible. Another method of modifying the characteristics of a polymer is to use a composition comprising of two or more types of alkyl cyanoacrylate monomers in combination with the appropriate inhibitors.

For example, a composition comprised of a monomer component comprising of 2-hexyl cyanoacrylate, hydroquinone, p-methoxyphenol and phosphoric acid; and a second component comprising of 2-hexyl cyanoacrylate polymer, gold, and ethyl myristate results in Polymer M. Alternatively, a composition comprised of a monomer component comprising of 90% n-hexyl cyanoacrylate and 10% methyl cyanoacrylate, hydroquinone, p-methoxyphenol and acetic acid; and a second component comprising of n-hexyl cyanoacrylate polymer, gold, and ethyl myristate, results in Polymer A.

A qualitative survey of Polymer M and A is shown in Table A. The physical characteristics disclosed are readily recognized by those of ordinary skill in the art as being relevant to the applications for which the polymers are used.

TABLE A (add to definitions section)

| Characteristics | Polymer M | Polymer A |
| --- | --- | --- |
| cohesion | excellent | excellent |
| adhesion | moderate - low | moderate - high |
| polymerization profile | polymerizes to semi-solid to soft-solid on contact with tissue or blood | polymerizes from liquid to soft solid to firm solid on contact with tissue or blood |
| tactile | rubbery/gummy | firm rubbery |
| molecular weight | low (1500 to 3000) | expected to be higher |
| inflammatory response | mild response | expected to be similar |
| viscosity | 14 to 15 centipoise | expected to be similar |
| radio opacity | yes | yes |
| exothermicity | low | expected to be slightly higher |

Polymers M and A have excellent cohesion properties. When introduced into a stationary fluid, or a fluid stream in motion, such as, the lumen of a blood vessel or other like passageway, the composition tend to stick together to itself remaining intact as a single mass or aggregate. This permits the polymers to be discretely deposited or placed at the desired location without the hazard of having potions of the composition breaking away and depositing at undesired locales. Polymers M and A appear to have viscosity properties that permit the injection of the liquid composition into a lumen of a blood vessel, duct, fistula or passageway in the body without using excessive pressure.

However, polymers M and A have different adhesion, polymerization and tactile properties. Polymer M is less adhesive than Polymer A, its polymerization profile upon contact with an anionic environment, such as, tissue or blood, is a transition from a liquid state to a semi-solid state before completing in a soft solid state, and the resultant polymer is a soft, rubbery, gummy solid. With these properties Polymer M is ideally suited for applications where the composition must penetrate further into anionic environment before arriving at the point of final placement. A preferred use is the treatment of arteriovenous malformations, also known as "AVM". Polymer M is also ideally suited for the treatment of longer type urinary fistulas, this is because preferred treatment requires greater penetration into cavity space by the liquid composition. Additional applications suited for Polymer M are creating a tubal occlusion, and surgical adhesions. For example, a composition of the present invention is applied to raw intraperitoneal tissue to prevent the tissue from adhering to itself or other tissue.

Polymer A is more adhesive than M, its polymerization profile upon contact with an anionic environment, such as, tissue or blood, is a transition from a liquid state to a soft solid and completing as a firm solid. With these properties Polymer A is ideally suited for applications where the composition must quickly adhere and polymerize in the surrounding anionic environment. Particularly advantageous applications for Polymer A is treatment of various types of aneurysms.

Another advantageous application for Polymer A is the treatment of fistulas, particularly those where it is desirable to have the resultant aggregate structure form close to the point of deployment.

Still another advantageous use for Polymer A is for the maintenance of homeostasis during surgery, such as, during hepatectomy, renal surgery, and during gynecologic tumor surgery.

Further, Polymer A can be used to treat certain types of varicose veins, where Polymer A is injected into the portal vein.

Utility

The present invention is useful for filling, occluding, partially filling or partially occluding an unfilled volume or space in a mass ("a space"). In particular, the composition is useful for filling an existing space, e.g., the lumen of a blood vessel, or the sac of an aneurysm, a space created by a transiently placed external device, e.g., a catheter or like device, a space created by a procedure, e.g., an excision or like procedure or implantation of an object, e.g., a stent or like device, or a space created by the composition; the composition is also useful for adhering tissue to tissue, or adhering tissue to a device. The composition has the property of polymerizing when it comes in contact with an anionic environment, or when it is deployed in situ in an existing space, e.g., the lumen of a blood vessel, or the sac of an aneurysm, a space created by a transiently placed external device, e.g., a catheter or like device, a space created by a procedure, e.g., an excision or like procedure or implantation of an object, e.g., a stent or like device, or a space created by the composition.

The present invention is useful as an embolic agent that selectively creates an embolic blockage in the lumen of a blood vessel, duct, fistula or other like body passageways.

The present invention can be prepared and maintained as a monomeric component and second component until needed. It has the ability to reliably and predictably change from a liquid state to a solid state, which is essential for its introduction and controlled placement into the lumen of vessel, duct, fistula or other like body passageways. The composition has low viscosity, which is essential for its administration by syringes and micro-catheters or other like devices.

The cohesive characteristics of the invention are such that when the composition in administered into an anionic fluid environment, such as blood, the composition forms a single aggregate structure. Additionally, the adhesive characteristics are such that the composition attaches to the lumen of vessel, duct, fistula or other like body passageways, but not to the degree where the device depositing the composition will become fixed to it before the practitioner can remove it.

The present invention causes mild tissue inflammation, sufficient to cause scarring, but not so severe to cause the formation of pus. Scar formation is desirable as the scar tissue is necessary to maintain the functionality of the embolic block after the composition has biodegraded, or otherwise eliminated from the lumen. The composition is sufficiently stable to biodegradation to allow for scarring to occur.

The present invention is radiopaque. Although this characteristic is not necessary for its function as an embolic agent, radiopacity allows the embolic block to be observed with x-ray or other such imaging techniques.

The rate of heat released during polymerization of the present invention is low enough such that the heat does not adversely effect surrounding tissues that may be heat sensitive, such as brain tissue.

The present invention and its biodegradation products are sufficiently non-histotoxic and non-cytotoxic so that its presence is well tolerated in the body.

The composition of the present invention is useful for filling, occluding, partially filling or partially occluding an unfilled volume or space in a mass ("a space").

The present invention provides a method for filling, occluding, partially filling or partially occluding an unfilled volume or space in a mass. The types of unfilled volumes or spaces within the scope of the present invention includes, but are not limited to the following instances.

For example, the present invention is used as a method of filling, occluding, partially filling or partially occluding an existing space, such as, a lumen of a passageway in the body, e.g., a blood vessel, a duct, an aneurysm, or a fistula. Examples of the types treatments covered by this method of use, include but are not limited to the following. The present invention is useful as a method of treating arteriovenous malformations (AVM) where the blood vessel(s) that feed the AVM are occluded thereby cutting off the blood supply to the AVM. The present invention is useful as a method to ablate diseased or undesired tissue by cutting off the tissue's blood supply. In particular, the present invention is useful as a method of treating a tumor having a discrete blood supply, where the blood vessel(s) that feed the tumor are occluded thereby cutting off the blood supply to the tumor resulting in diminished growth or death of the tumor. The present invention is useful as a method of preventing or mitigating the development of an aneurysm by creating a partial occlusion at a location in the blood vessel selected to modify the fluid dynamics within the vessel to mitigate the formation or development of an aneurysm. The present invention is useful as a non-surgical method of treating symptomatic uterine leiomyomas by embolizing/occluding the uterine artery. This method has been reported using a non alkyl cyanoacrylate composition in the *Journal of Vascular and Interventional Radiology,* 10:891–894, July–August 1999. The present invention is useful as a method of sterilizing a female mammal by occluding the fallopian tubes thereby preventing the passage of the eggs from the ovaries to the uterus. The use of an occluding agent to sterilize a female mammal is disclosed in U.S. Pat. No. 5,989,580 "Method of Sterilizing Female Mammals," herein incorporated by reference. The methods disclosed in this patent can be advantageously applied using the compositions of the present invention, and are within the scope of the present invention.

The present invention is an embolic agent that provides a method for selectively creating and placing an embolic blockage which mechanically blocks, totally or partially, the lumen of a blood vessel, duct, fistula or other body passageway. In particular, the current invention is particularly useful in blocking, totally or partially, or diverting the flow of blood through the lumen.

The present invention can be advantageously used to block blood flow to certain tissues or areas. For example, the present invention can be used to treat arteriovenous malformation (AVM). An AVM is a collection of abnormal blood vessels which are neither arteries or veins. These vessels are packed closely together to form the nidus of the AVM. Blood flow into the AVM nidus is through thinned, enlarged, tortuous vessels and is rapidly shunted into draining veins because the nidus contains no arterioles or capillaries to provide high resistance. Clinical symptoms experienced because of AVMs are bleeding, re-direction of blood from nearby normal structures, or seizures. The primary clinical problem associated with cerebral AVM is the potential for lethal hemorrhage. The current standard of care for treating AVMs is surgical removal, high energy radiation or embolization with particular devices.

Further, the present invention can be used for treating cancer by diverting or blocking blood flow to tumors, the present invention is particularly useful for treating tumors in areas that are not easily accessible for surgical intervention, for example, brain tumors.

Other advantageous uses of the present invention are for aortopulmonary closure; treatment of artery pseudoaneursym; hepatic artery vascular occlusion and for temporary vascular occlusion during co-administration of cytotoxic drugs; treatment of other types of vessels, for example, the composition can be used for creating tubal occlusions, fallopian tube occlusions, vas deferens occlusions, and urinary occlusions.

The present invention provides a method of filling, occluding, partially filling or partially occluding a space created by a transiently placed external device, such as, a catheter balloon. Examples of the types of treatments covered by this method of use include, but are not limited to the following. The present invention is useful as a method of treating an aneurysm by filling the space within the aneurysm with a composition of the present invention, where the composition polymerizes in the space within the aneurysm, thereby preventing the rupture of the aneurysm. This treatment can be effected using the present invention with any number of catheters, catheter coils, catheter wires or catheter balloons commercially available. Examples of such devices are commercially available from sources. For instance, Micro Therapeutics, Inc., 2 Goodyear, Irvine, Calif. 92618, markets a line of medical devices, such as, the Rebar™ Micro Catheter, Equinox™ Occlusion Balloon System and SilverSpeed™ guidewires. Similarly, U.S. Pat. No. 5,882, 334 "Balloon/delivery Catheter Assembly with Adjustable Balloon Positioning," assigned to Target Therapeutics, Inc., and incorporated herein by reference, is directed to a catheter assembly for delivering compositions, such as, those of the present invention.

The present invention also provides a method of filling, occluding, partially filling or partially occluding a space created or resulting from a procedure, such as with the excision of tissue, or insufflation. Examples of the types of treatments covered by this method of use include, but are not limited to the following. The present invention is useful as a method of treating oozing capillaries following an excision procedure.

The present invention further provides a method of filling, occluding, partially filling or partially occluding a space created by the placement or implantation of an object, such as, a medical device. Examples of the types of uses covered by this method of use include, but are not limited to the following. The present invention is useful as a method of restoring the normal fluid dynamics at the peripheral edges of a vascular stent by filling the dead spaces between the stent and the lumen wall created by the implantation of the stent.

Still another advantageous use is the controlling and smoothing the blood flow around stents. A major complication from the balloon angioplasty and the use of stents is disruption of the smooth flow of blood past and around the stent which can lead to the formation of blood clots and their associated complications. The composition of the present invention can be used to modify and make regular the slip streams of blood through and adjacent to the stent to mitigate or alleviate the cause of the turbulence, and such turbulence causing states.

The present invention further provides a method of filling, occluding, partially filling or partially occluding a space created by the composition itself, such as, where the composition is used as a bulking agent. Examples of the types of uses covered by this method of use include, but are not limited to the following. For example, a method of recreating normal external contours, such as following physical trauma.

Administration

The monomer component and second component of the present invention are combined just prior to use. The composition of the present invention is administered using any type of deployment device. The term "deployment device" refers to a device used to deploy fluids or compositions similar to those of the present invention, such as, a needle, catheter devices, catheter balloon, stereotaxic placement devices, or the like. Methods for using these devices are readily known to one of ordinary skill in the art, and such devices are commercially available. Such devices and methods are readily known to those of ordinary skill in art. For example in U.S. Pat. No. 5,925,683 "Liquid Embolic Agents", herein incorporated by reference, there is disclosed a method for introducing liquid embolic agents/solutions into the human body to form precipitated embolic occlusion masses, and also how this method is used for treating hepatic tumors using portal vein embolism. In U.S. Pat. No. 5,702,361 "Method for Embolizing Blood Vessels", herein incorporated by reference, there is disclosed a method of embolizing a vascular site in a patient's blood vessel comprising of introducing, via a catheter, at the vascular site to be emobolized a non-particulate agent or a plurality of such agents, and delivering, via a catheter, to said vascular site a polymer composition comprising a biocompatible polymer, a biocompatible solvent and contrast agent, wherein the delivery is conducted under conditions where the polymer precipitate forms in situ at the vascular site resulting in the embolizing of the blood vessel and where the non-particulate agent is encapsulated within the precipitate. Additional devices applicable to the present invention are those disclosed in U.S. Pat. No. 5,882,334 "Balloon/delivery Catheter Assembly with Adjustable Balloon Positioning," incorporated herein by reference, directed to a catheter assembly for delivering compositions. Further, Micro Therapeutics, Inc., 2 Goodyear, Irvine, Calif. 92618, markets medical devices, such as, the Rebar™ Micro Catheter, Equinox™ Occlusion Balloon System and SilverSpeed™ guidewires, that are approved by the U.S. Food and Drug Administration for use in treating conditions such as those within the present invention.

The composition of the present invention are administered with any type of commercially available needle, catheter devices, or stereotaxic placement devices, preferably in conjunction with imaging technology that provides the practitioner with guidance as to the placement of the composition. The compositions of the present invention can be used advantageously in conjunction with any embolization method that employs an embolizing agent, occluding agent, or such composition that creates an embolic block, or occlusion, or otherwise in effect is used for filling, occluding, partially filling or partially occluding an unfilled volume or space in a mass ("a space"). Delivery can also be made with a micro catheter made from or coated with an agent that lessens the likelihood of accidental gluing of the device to the vessel, for example, hydrophilic coating and silicone derivative coatings.

EXAMPLES

The following examples are given to enable those of ordinary skill in the art to more clearly understand and to practice the present invention. The examples should not be considered as limiting the scope of the invention, but merely as illustrative and representative thereof.

Example 1

Preparation of 2-Hexyl Cyanoacetate

A 5 liter, 24/40 ground glass jointed flask was configured with a reflux condenser, Dean-Stark trap, and football magnetic stirring bar. The reaction vessel was charged with the 1,275.0 g of cyanoacetic acid (Aldrich Chemical Co.), 1,581.5 g of 2-hexanol (Aldrich Chemical Co.) and 3.0 g of p-toluenesulfonic acid (Aldrich Chemical Co.), and 1,500 of toluene (Aldrich Chemical Co.). The reaction mixture was stirred and heated to reflux. Water was formed as a byproduct of the reaction and was collected during the course of the reaction. The reaction was continued until there was a period of over 30 minutes where no water was produced. The amount of water collected was 230 ml and indicated that the reaction had completed with a 85.2% theoretical yield. The reaction mixture was allowed to cool to room temperature.

The reaction mixture was stirred and 500 ml of a saturated baking soda (sodium bicarbonate) solution was gradually added to the mixture. The reaction mixture was stirred vigorously until the frothing stopped. The reaction mixture was poured into a six liter separatory funnel, to which an additional 500 ml of water was added. The funnel was vigorously agitated. The aqueous phase was separated and saved as Reaction Water. The pH of the aqueous layer was measured to insure that the pH was over 8. Another 500 ml of water was added to the organic phase reaction mixture in the separatory funnel. The contents of the funnel were again agitated, the aqueous and organic phases were allowed to settle, and the aqueous phase separated and also saved as Reaction Water. This washing procedure was repeated two additional times. The organic phase was moved to a 5-liter flask. The flask was configured with a distillation condenser. The reaction mixture was heated to reflux, and the remaining water was separated from the mixture and discarded. The apparatus was reconfigured for vacuum fractional distillation. Initially, the toluene and 2-hexanol in the mixture were removed by reducing the pressure of the apparatus to about 5 Torr, and then by heating the mixture to 600 with stirring. After the solvents were removed, the pressure was further reduced to less than 1 Torr and gradually increased heat until the desired 2-hexyl cyanoacetate began to distill off. The heat was adjusted so that the product was recovered at a rate of 2 drops/sec. The recovery collected 1921.1 g (70.76% yield) of the 2-hexyl cyanoacetate, and was halted when no more material came out of the distillation unit. Gas chromatographic analysis of the purity of the 2-hexyl cyanoacetate indicated that the product was 98.3% pure, which was well above 95% purity requirement for proceeding to the next procedure.

If the purity of the 2-hexyl cyanoacetate had been below 95%, the material could have be purified by vacuum distillation, or using any like technique for purification known to those of ordinary skill in the art.

Example 2

Preparation of 2-Hexyl Cyanoacrylate

A 5-liter three-necked flask was configured with a reflux condenser, Dean-Stark trap, an addition funnel and a mechanical stirrer with a glass paddle in a 5-liter heating mantle. Paraformaldehyde 272.4 g and methanol 1,500 ml were combined in the flask. The reaction mixture was heated to reflux and stirred for a period of 1 hr until the solution began to cleared. 3 ml of piperidine was washed into the reaction mixture with methanol, followed by 1521.9 g of 2-hexyl cyanoacetate added in a dropwise fashion. The resulting reaction was exothermic, and the heat was adjusted to maintain the reaction mixture at reflux temperature. The reaction mixture was refluxed for an additional 30 minutes after the conclusion of the addition. Methanol was distilled from the reaction mixture and collected through the Dean-Stark trap until 1420 ml of the original methanol (98%) was recovered (compensating for spillage). The reaction mixture was halted overnight at this point.

The reaction vessel was configured with a vacuum apparatus to collect residues, and placed under high vacuum to remove remaining volatile materials. The vacuum was gradually increased until less than 10 Torr was reached. The apparatus was heated until all the solvent had been removed. Once the solvent was removed, 75 g of phosphorous pentoxide was added to the mixture taking care to minimize its exposure to air. The heat was discontinued, and the mixture was stirred for one hour. The apparatus was then flooded with sulfur dioxide. The pressure was reduced to less than 10 Torr and heated slowly, the flow of sulfur dioxide was adjusted for a constant low-level flow of gas into the apparatus.

A 1 liter flask was washed with concentrated sulfuric acid, three times with water, and once with ultra pure water. The flask was oven dried for one hour at 110° C. and was allowed to cool to room temperature. 10 drops of 85% phosphoric acid and approximately 25–50 mg of hydroquinone was added to the 1 liter flask. The flask was fitted as the receiver flask to the distillation apparatus. The pressure of the distillation was reduced to less than 10 Torr. The reaction mixture was heated and stirred until the distillation began. 418 g of 2-hexyl cyanoacrylate was collected at a 25% yield. The distillation was halted when the temperature rose above 110° C.

Example 3

Purification of 2-Hexyl Cyanoacrylate

The 2-hexyl cyanoacrylate was purified in a two step process. The compound was first by vacuum distillation, and then further purified by spinning band column.

Vacuum Distillation

A vacuum distillation apparatus was configured with a 2 L flask, magnetic stirrer, fraction cutter, a 10" Vigreux column a clasien head, condenser, thermometer and a 100 ml forecut receiving flask. 10 drops of 85% phosphoric acid and 10 mg of hydroquinone was added to the forecut flask. The unpurified 2-hexyl cyanoacrylate was place into the distillation flask and the pressure of the unit was reduced to just under 1 Torr. The material was stirred and gradually heated until product was being distilled and collected at a rate of one drop per minute. After 35 ml of distillate was collected, a second 2 L receiving flask that had been prepared by acid washing, followed by the addition of 25 drops of 85% phosphoric acid and 20 mg hydroquinone was placed to receive the distillate. The distillation rate was gradually increase till the product was being collected at a rate of 2–3 drops per second. When the distillation head temperature rose 2° C. above that used to collect the main fraction, the distillation was completed. Heat was d discontinued, and the material was allow to cool under dry air by air filtered through a drying tube.

Spinning Band Column Purification

The spinning band column (B/R Instrument Corp., 9119 Centreville Road, Easton, Md. 21601, Model 9600) is a long jacketed silvered column fitted with a 30/50 socket joint at the bottom. A magnetic stirring bar was added to the 5 L socket joint flask, which was then filled with the product to be purified. A heating mantle is supported on a magnetic stirrer that is raised and lowered with a laboratory jack to fit to the column. On the upper right hand side of the column there was another 30/50 male socket joint for a 100 ml receiving flask. All flasks and joints were greased with high vacuum grease to assure a good vacuum seal. When assembled, a glass temperature probe was inserted into the 10/15 joint of the flask, and a metal Tempora probe was inserted inside the glass probe. The 29/42 joint containing the stopcock was greased and placed into the flask and connected to a sulfur dioxide gas line. The pressure of the system was gradually reduced down to just under 1 Torr of pressure.

Operation of the spinning band column was controlled by a microprocessor. The column was programmed to operate under the following conditions, the water cooling temperature was set to 15° C., the column's motor turns on at 24° C., equilibration time was 2 min, open temperature 28° C., close temperature 90° C., mantle rate 24° C., reflux ratio 20 to 1 and pot temperature to end run 90° C. Just prior to beginning the distillation a small flow of sulfur dioxide was leaked into the system. The temperature of the flask was monitored during the distillation to ensure that the temperature at no time rose above 100° C. The distillate was collected in the receiver flask at the end of the distillation.

The contents in the flask of the spinning band column were allowed to cool for 30 min. A second high vacuum distillation apparatus configured identically to the vacuum distillation apparatus first used in this procedure was setup using a 2 L round bottom flask. To this flask was added 0.0269 g of hydroquinone, 0.0275 g of p-methoxyphenol, and 0.0794 g of phosphoric acid. The residue for pot of the spinning band column was added to the 2 L round bottom flask of the vacuum distillation apparatus. The contents of the flask was stirred and the pressure of the unit was reduced to just less than 1 Torr. A small stream of sulfur dioxide was leaked into the apparatus as the distillation continued. A receiver flask was prepared by adding 10 mg hydroquinone and 15 drops of 85% phosphoric acid. A forecut fraction of 86.3 g was collected at the rate of 2–6 drops per minute. The main fraction was collected in a receiver similarly prepared as the forecut fraction flask. 1620.1 g of main fraction product was collected at a rate of 20–25 drops per minute. The material was then re-distilled by the spinning band column under the previous conditions.

The purity of the 2-hexyl cyanoacrylate was determined by gas chromatography. The gas chromatograph was configured as follows,

| HP 5890 Gas Chromatograph with HP Chemstation Software. | |
| --- | --- |
| Column Description: | Supelco Nukol (60 meter, I.D.-0.32 mm, film thickness-1 micron). |
| Instrument Parameters: | Method 1 |
| Injector Temperature: | 220° C. |
| Detector Temperature: | 280° C. |
| Head Pressure: | 15 PSI |
| Air Pressure: | 35 PSI |
| Hydrogen Pressure: | 20 PSI |
| Aux: | 60 PSI |
| Initial Oven Temperature: | 140° C. for 20 min. |
| Ramp: | 5° C./min. |
| Final Oven Temperature: | 200° C. for 50 min. |
| A Splitless System. | |
| Injection Volume: | 1.0 micro liter |

1.0069 g of the 2-hexyl cyanoacrylate was mixed thoroughly with 2 drops of 1-hexanol (0.0044 g), was analyzed and impurities were found to be at an acceptable for use. The 2-hexyl cyanoacrylate was sufficiently pure to use for product.

Example 4

Formulation of the Monomer Component

The monomer component was formulated with the following materials 2-hexyl cyanoacrylate 1249.9 g, hydroquinone 0.0764 g, p-methoxyphenol 0.0874 g and phosphoric acid 0.1693 g. The hydroquinone and p-methoxyphenol were kept under reduced pressure in a desiccator over a drying agent. The pure phosphoric acid was particularly deliquescent and care was taken not permit water contamination. The calculated molar quantities and PPM of each material were as follows,

| Material | Moles | PPM |
| --- | --- | --- |
| 2-hexyl cyanoacrylate | 6.8964 | 999,547 |
| hydroquinone | 0.000694 | 100 |
| p-methoxyphenol | 0.000704 | 102 |
| phosphoric acid | 0.001726 | 250 |

Overall purity of the formulation was determined by gas chromatograph to be less than 1%, using 1-hexanol as an internal standard.

| Instrument Description: | HP5890 Gas Chromatograph with HP chemstation software. |
| --- | --- |
| Column Description: | Supelco Nukol (60 meters-length, I.D., 0.32 mm, Film Thickness 1 micron) |
| Instrument Parameters: | Method 1 |
| Injector Temperature: | 220° C. |
| Detector Temperature: | 280° C. |
| Head Pressure: | 15 PSI |
| Air Pressure: | 35 PSI |
| Hydrogen Pressure: | 40 PSI |
| Aux.: | 60 PSI |
| Initial Oven Temperature: | 140° C. for 20 min. |
| Ramp: | 5° C./min. |
| Final Oven Temperature: | 200° C. for 50 min. |
| A Splitless System: | |
| Injection Volume: | 1.0 microliter |

Example 5

Preparation of the 2-Hexyl Cyanoacrylate Polymer Component ("The Second Component")

Ethyl myristate was obtained commercially from Aldrich Chemical Company at 97% purity. Prior to use, the ethyl myristate was further purified by vacuum distillation to 99.8% purity following standard routine chemical procedures.

Six 3 ml syringes were fill with purified 2-hexyl cyanoacrylate. 500 mg of sodium bicarbonate and 250 ml of ultra pure water were placed into a Waring blender. The lid of the blender was adjusted so that the contents of the syringes could be emptied dropwise into the center of blender while the blender was stirring. With the speed of the blender set to high, each of the syringes were emptied in a dropwise fashion into the stirring blender. When the addition was completed, the lid of the blender was closed and the mixture was stirred for another minute. The solution was decanted from the blender leaving just solid material in the blender. Residual solid material that was inadvertently removed with the decanted solution was recovered by filtration, washed with ultra pure water and placed back into the blender. Solid material adhering to the inside portion of the blender was rinsed with ultra pure water back with the rest of the solids in the blender. An additional 250 ml of ultra pure water was added into the blender, and the water and solid mixture was blended for 1 minute. Following the last procedure, water solution was decanted through a large coarse fritted glass funnel filter that recovered solid material in the solution. The solid material was washed with methanol prior to be added back to the rest of the solid material. The walls of the blender were rinsed with methanol to collect all the solid material back into the blender. 250 ml of Methanol was added to the blender. The solids were blended for one minute. The solid material is filtered from the methanol. Any residual solid material in the blender is washed with methanol and combined with the solid material filtered from the methanol. The solid material on the filter was placed under a low vacuum to remove the rest of the methanol. The solid material was moved quantitatively to a 100 ml round bottom standard tapered flask. The flask was placed under reduced pressure to remove the remaining methanol. 2 g of the solid material was combined with 100 g of powdered gold. The mixture was placed into a standard laboratory blender and blended for one minute. The blender was agitated constantly during the blending to ensure that the gold did not settle during the blending. 1.020 g portions of the blended material were placed into previously cleaned and prepared bottles. To each bottle was added 500 mg of ethyl myristate at 99.8% purity. The filled bottles were kept under a Laminar flow hood. The unsealed bottles were arranged in trays for immediate ethylene oxide sterilization by Sharp Coronado Hospital, Sterile Processing Department under standard conditions.

Example 6

Comparison of Catheter Adhesion Force for 2-Hexyl Cyanoacrylate (Neuracryl M) and n-Butyl Cyanoacrylate (Histoacryl) Compositions The present invention is also known by the name of Neuracryl M, where Neuracryl M1 corresponds to the monomer component, and Neuracryl M2 corresponds to the second component comprising of the gold coated 2-hexyl acrylate. This example demonstrates differences in adhesion between the two cyanoacrylates by measuring the amount of force required to remove a catheter from various compositions of Neuracryl and Histoacryl. Histoacryl is commercially available from Braun GmbH. It is similar to Neuracryl M in that it is a polymer composition also based on a cyanoacrylate structure, i.e., n-butyl cyanoacrylate. However, the force required to withdraw a catheter from Histoacryl is greater than that required for Neuracryl M, and in this key aspect, Neuracryl M possesses a surprising and unexpected advantage over Histoacryl.

The force resulting from catheter adhesion was determined for Neuracryl M1 and M2 (mixed), pure Neuracryl M1, Neuracryl M1 mixed with 33% Ethiodol, Neuracryl M1 mixed with 50% Ethiodol, pure Histoacryl, Histoacryl mixed with 33% Ethiodol, and Histoacryl mixed with 50% Ethiodol were measured and compared.

All the mixtures were injected through a TurboTracker micro catheter device (Medi-tech/Boston Scientific, Watertown, Mass.). All mixtures were prepared immediately prior to use to prevent separation of the components or contamination. The catheter tips were placed at the bottom of 10 mm deep by 5 mm diameter wells filled with 0.2 mL of heparinized human whole blood. Through the micro catheter, 0.15 mL of each embolic mixture was injected into each well, surrounding the tip of the micro catheter. Mixtures containing Histoacryl were allowed to polymerize for 1 minute, and those containing Neuracryl for 3 minutes. The microcatheters were then extracted from the polymerized cyanoacrylates at a constant speed of 8.3 mm/sec (Model 1000 Materials Testing System; Instron, Canton, Mass.) and the forces required for extraction were measured and recorded (Minibeam Force Transducer, 25-lb capacity; Interface Advanced Force Measurement, Scottsdale, Ariz.). Five samples of each mixture were tested. Comparison of the results was performed using the Student t test.

Successful mesurements of the peak forces required for the extraction of the catheters from the polymerized cyanoacrylates were obtained for six of the seven mixtures tested. A wide range of peak forces were required to extract the microcatheters from the various mixtures. The force of extraction for the Neuracryl M1 and 50% Ethiodol mixture was less than 0.05 Newtons and beyond the ability of the apparatus to obtain precise measurements. The peak forces required to extract the microcatheters from either Histoacryl mixed with 33% Ethiodol (1.44 N±0.33) were significantly higher ($P<0.01$; $P<0.05$) than those for pure Neuracryl M1 (1.00N±0.23). Histoacryl had to be mixed with 50% Ethiodol to decrease the force of extraction (0.34N±0.14) to less than that associated with pure Neuracryl M1 ($P<0.01$).

When Neuracryl M1 and M2 were mixed together the force required for micro catheter extraction (0.41N±0.14) was significantly lower than that for either pure Histoacryl (1.83 N±0.21), Histoacryl mixed with 33% Ethiodol (1.44 N±0.33), or Neuracryl M1 alone (1.00 N±0.23) ($P<0.01$; $P<0.01$; $P<0.01$, respectively). The force required to extract microcatheters from the Neuracryl M1 and M2 mixture was not, however, significantly different from that of Histoacryl mixed with 50% Ethiodol (0.41 N±0.14 vs. 0.34 N±0.14)

Although Neuracryl M1 was not designed to be mixed with Ethiodol, like Histoacryl, Neuracryl M1 demonstrated markedly decreased micro catheter adhesion when mixed with 33% and 50% Ethiodol. The extraction force was reduced significantly from 1.00 N±0.23 to 0.28 N±0.12 when Neuracryl M1 was mixed with 33% Ethiodol ($P<0.01$). There was no significant difference between the peak extraction forces for Neuracryl M1 mixed with 33% Ethiodol and Neuracryl M1 and M2 mixed was intended for clinical use. (0.28 N±0.12 vs 0.41 N±0.14). When Neuracryl M1 was mixed with 50% Ethiodol, the force of extraction was less than 0.05 N and below our limit for accurate measurement. The force was so low that, unlike with the other mixtures, no effacement of the slight natural curve of the catheter was observed prior to the tip of the catheter pulling out of the cyanoacrylate.

Example 7

Comparison of 2-Hexyl Cyanoacrylate and n-Butyl Cyanoacrylate Interactions with Blood and in an Arteriovenous Malformation Model The following example compares the interaction of 2-hexyl cyanoacrylate composition of the present invention (2HCA) and a composition of 33% n-butyl cyanoacrylate and 66% ethiodol (NBCA), which is the clinical standard, with blood.

2HCA was compared to NBCA in heparinized pig blood under four conditions:

(1) a drop of each composition was placed on the surface of blood, observed, and the polymerization process was timed.

(2) a 22 gauge needle was placed below the surface of static blood, and 0.4 milliliter of each composition was injected and observed over a 1 minute period;

(3) blood was circulated through a 4 millimeter I D polyvinyl chloride tubing at 40 centimeters per second. A 22 gauge needle inserted into the central slipstream introduced the compositions at rates varying from 0.1 ml to 8 ml per second powered by a Medrad mk 4 pressure injector. Behaviors were recorded via fluoroscopy on S VHS T V;

(4) standardized arteriovenous malformation models were placed in a circuit of pulsatile flowing blood, and the compositions were introduced via microcatheters under direct fluoroscopic control, using the same techniques used in humans. The models were later opened, the polymerized compositions were removed and their characteristics were compared. Polymer which escaped from the models were also collected downstream and examined.

Findings (1) Dropping the compositions onto the surface of blood yielded generally equal polymerization times, about 2 seconds.

(2) When injected below the surface of static blood, the 2HCA formed a rubbery elastic mass which remained at the needle's tip. The NBCA compound fell away from the needle, to the bottom of the beaker and polymerized to a friable mass.

(3) When injected into blood flowing at physiologic velocities, the NBCA compound formed small, individual, nearly spherical droplets that did not remain as a cohesive mass, but rather broke away and embolized down stream. There was no injection rate at which we could keep the device from embolizing away, or to make it block the tube. Conversely, there was no rate of injection which could prevent the 2HCA from remaining as a cohesive polymerized mass and the tube was blocked solidly for the length of the injection.

(4) When injected into the AVM model, the 2HCA yielded significantly better penetration than the NBCA compound. The character of the polymerized compositions was significantly different: the NBCA compound made a firm yet friable mass much like dry cottage cheese; the 2HCA mass was elastic much like chewing gum.

In summary, the standard test of the cyanoacrylate drop on blood yielded no predictive information. However, when the cyanoacrylates were respectively injected below blood, strikingly different outcomes were observed. The NBCA immediately fell away from the needle to the bottom of the beaker, whereas the 2HCA remained as a cohesive whole at the needle tip. There was no introduction rate which could disrupt the cohesiveness of 2HCA; there was no introduction rate which allowed the NBCA composition to remain a cohesive whole. Particles of the NBCA composition formed and continually pushed downstream. Injection of 2HCA into standard AVM models yielded consistently better control penetration of the nidus of the AVM.

Example 8

Preparation of n-Hexyl Cyanoacetate

The following is a scaled up procedure that can be used for preparing manufacturing quantities of n-hexyl cyanoacrylate. This prospective procedure is based on a smaller scale laboratory bench top synthesis used for preparing n-hexyl cyanoacrylate, and procedures developed employed for preparing 2-hexyl cyanoacrylate, as were taught in the preceding examples.

Equip a 50 liter resin flask with 29/42 ground glass jointed bulbed reflux condenser, a 100 ml Dean-Stark trap and mechanical stirring. To the flask is added 150 moles (12, 754.8±10 g) of Cyanoacetic acid, 150.5 moles (15,810±10 g) of n-hexanol, ten liter (10,000±20 ml) of toluene, and 10 grams (10±0.1 g) of p-toluenesulfonic acid. The mixture is heated until homogeneous. The heat is removed, and the mixture is allowed to stand for 4 days.

After 4 days, the mixture is heated over a period of five hours to boiling. Water is collected and measured in the Dean-Stark trap as it is formed. The distillation is stopped after 8 to 10 hours and allowed to sit overnight. The next day the same exact process is repeated to get the mixture to boiling. To the mixture is added 10±0.01 g of p-toluenesulfonic acid with stirring. As with the previous day, water is collected and measured in the Dean-Stark trap as it is formed. The heat is removed after 8 to 10 hours and the mixture is allowed to cool overnight. The following morning, while the mixture is stirred, 5 liters of a saturated baking soda solution is gradually added. Tap water can be used for preparing the saturated baking soda wash solution. The mixture is stirred while continually added the saturated baking soda solution until the frothing stops. The pH of the aqueous solution should be above 9.

A filter flask configured with a vacuum attachment is used to transfer the mixture quantitatively from the 50 liter flask into a series of eight 6-liter separatory funnels with approximately 4 liters in each funnel. Add 1 liter of tap water to each funnel, seal and shake vigorously several times. Allow the funnel to set in the stand until the aqueous and organic layers separate. The water is removed from the mixture and saved. The pH of the organic layer is measured, if the pH is less than 8, add 500 ml of saturated baking soda to the organic solution in the funnel, seal and shake vigorously several times.

Another 1 liter of water was added to each funnel. The funnel were sealed and shaken vigorously. The mixture was allowed to settle until the aqueous and organic layers separated. The aqueous layer was removed as before and its pH measures, and then added to the aqueous layer saved from the previous wash. The pH should be above 7. This procedure was repeated two more times for a total of four times. This procedure was repeated for each separatory funnel.

After the washes, the organic layers of each funnel is combined in a 50 liter reaction flask equipped as Apparatus A. The save aqueous layers from the washes are then added back to the separatory funnels and allowed to separate again. The organic layer from the funnels is added to the combined organic layer in Apparatus A. The pH of the aqueous wash solution is measure, if the pH is above 7 the solution can be disposed.

The organic solution in Apparatus A is heated to reflux. Water from the reaction is collected and discarded. The apparatus is reconfigured for a distillation procedure. Under vacuum and heat, the toluene removed from the reaction solution. The toluene that is removed will contain some amount of n-hexanol. The reaction apparatus is re-configured for high vacuum distillation procedure. With stirring and with pressure reduced to just under 5 Torr, additional amounts of solvent are removed from the solution. The pressure is further reduced to just less than 2 Torr. Using a 500 ml flask, about 300 to 400 ml of the forecut is collected. The temperature will climb and level to about 60° C. The temperature will vary according to the actual pressure. When the distillation temperature is constant for 10 minute, the forecut flask is replaced with a 22.4 collection flask. The distillation is continued under reduced pressure of about 2 Torr. When the distillation is completed, the recovered n-hexyl cyanoacetate is purified.

The n-hexyl cyanoacetate is placed in a 22.4 liter resin flask with a mechanical stirrer, glass paddle, reflux column, condenser and fraction cutter on two interlocking movable platforms. The pressure in the apparatus is reduced, and the material is slowly stirred with a slow gradual increase in temperature. The gradual increase in temperature is continued until the product has moved up the distillation column up to the point of distillation. As distillation material is collected, about 200 ml of the forecut is collected at a slow rate. The collection flask is replaced with a 22.4 liter round bottom receiver into which the distilled n-hexyl cyanoacetate is collected. The purity of the n-hexyl cyanoacetate is determined using gas chromatography.

Column Description: Supelco Nukol (60 meters, 0.32 mm-column thickness, 1.00 micron film thickness.
Integrator Program: Ar Rej 1000, Peak Wd 0.20

| Gas Chromatograph Program: | |
|---|---|
| Initial Temperature | 140° C. |
| Initial Time: | 20 minutes |
| Ramp Speed: | 5° C./minute |
| Final Temperature | 200° C. |
| Final Time: | 52 minutes |
| Detector Temperature: | 280° C. |
| Injector Temperature: | 220° C. |
| Detector: | Flame Ionization |
| Injector Volume: | 1.0 microliter with simultaneous start up. |

Example 9

Preparation of n-Hexyl Cyanoacrylate

The following is a scaled up procedure that can be used for preparing manufacturing quantities of n-hexyl cyanoacrylate. This prospective procedure is based on a smaller scale laboratory bench top synthesis used for preparing n-hexyl cyanoacrylate, and procedures developed employed for preparing 2-hexyl cyanoacrylate, as were taught in the preceding examples.

A 22.4 liter, 29/42 ground glass jointed three neck Resin flask is equipped with a reflux condenser, Dean-stark trap, an additional funnel and a mechanical stirrer with a glass paddle. The following materials are added to the flask, 1,357.1±1.0 g (45.2 moles) of paraformaldehyde, 12,500±10 ml of methanol and 10 ml of piperidine. A small amount methanol is used to washed into the reaction mixture. The reaction mixture is heated with stirring to reflux. After refluxing for one hour, the heat is removed and 7615.4±1.0 g (45 moles) of n-hexyl cyanoacetate is added. The reaction is exothermic and the rate of addition is adjusted to maintain the reflux without flooding the condenser. The reflux is continued for an additional 30 minutes after the completion of the addition of n-hexyl cyanoacetate. The methanol from the reaction flask is collected by distillation through the Dean-stark trap. The amount of methanol collected is measured and compared with the amount initially added to the reaction mixture, when 11,875 ml (95%) of the methanol was collected the heat was turned off.

A 1 liter round bottom receiver is fitted to the bottom of the distillation apparatus. The system is placed under high vacuum with a gradual increase in heat. Additional volatile materials are collected. Heat is removed and the apparatus is re-pressurized with air.

While the reaction mixture is stirred, 400 g of phosphorous pentoxide is added to it through a powder funnel. Exposure of the phosphorous pentoxide to air should be kept to a minimum. Upon completion of the addition, the apparatus was immediately closed to exposure to air. The reaction mixture is stirred for 30 minute and the pressure in the apparatus reduced to less than 10 Torr. The reaction mixture is gradually heated until the reaction began. A very slow flow of sulfur dioxide is introduced into the vacuum system. As the distillation began, no forecut is collected, rather all the materials are collected into a 2 liter receiver. This receiver is prepared by washing it with concentrated sulfuric acid and then three times with tap water followed with a final wash with Ultra pure water. The flask is dried in an oven at 100° C. for one hour. Allow the flask to cool to room temperature. Add 40 drops of 85% phosphoric acid and approximately 100 mg of hydroquinone. Place the prepared receiving flask in the distillation apparatus while maintain the vacuum in the system. Collect the product until the pressure cannot be maintained and the temperature of the distillate increases by 10° C. above that for the main collection of the fraction. The distillate is analyzed for purity by gas chromatography according to the following conditions.

| Instrument Description: | HP5890 Gas Chromatograph with HP Chemstation software |
|---|---|
| Column Description: | Supelco Nukol (60 meter, I.D.- 0.32 mm, film thickness 1.0 micron |
| Instrument parameters: | Method 1 |
| Injector Temperature: | 220° C. |
| Detector Temperature: | 280° C. |
| Head Pressure: | 15 PSI |
| Air Pressure: | 35 PSI |
| Hydrogen Pressure: | 20 PSI |
| Aux.: | 60 PSI |
| Initial Oven Temperature: | 140° C. for 20 minutes |
| Ramp: | 5° C./minute |
| Final Oven Temperature: | 200° C. for 50 minutes |
| Split less system | |
| Injection Volume: | 1.0 micro liters |

Example 10

Purification of n-Hexyl Cyanoacrylate by Distillation

The following is a scaled up procedure that can be used for preparing manufacturing quantities of n-hexyl cyanoacrylate. This prospective procedure is based on a smaller scale laboratory bench top synthesis used for preparing n-hexyl cyanoacrylate, and procedures developed employed for preparing 2-hexyl cyanoacrylate, as were taught in the preceding examples.

Prepare an apparatus for high vacuum distillation using magnetic stirring, a fraction cutter, a two liter flask, a 10" Vigreux column, a Claisen head, condenser, thermometer and a 500 ml forecut receiving flask. About 30 mg of hydroquinone and add ti to the forecut receiving flask. Add 25 drops of 85% phosphoric acid to the receiving flask. Add the n-cyanoacrylate from the previous example to the distillation flask. The pressure of system is reduced to less than 2 Torr.

Begin heating the stirring pot and adjust the heating so that the rate of the distillation is controlled to about 2 to 3 drops per minute. Collect about 250 ml of the material in the forecut flask. Add approximately 25 drops of 85% phosphoric acid and approximately 25 mg of hydroquinone to an acid washed 3 liter receiving flask. A small amount of the hydroquinone and 85% phosphoric acid is left in the receiving flask to avoid polymerization of the distillate. The receiver is attached to the distillation apparatus without losing vacuum. The distillation is continued. The main fraction is collected at a rate of about 1 drop/second. When the distillation head temperature has risen 2° C. above that used to collect the main fraction, the distillation is discontinued by shutting off the heat and allowing dry air to be filtered through a drying tube into the high vacuum of the system. This phase of the distillation should require 4 to 6 hours to complete.

The product placed into a 5 liter socket jointed flask with a magnetic stirring bar. The flask is fitted onto spinning band column. A heating mantle is supported on a magnetic stirrer that is raised and lowered with a laboratory jack to fit to the column. A 250 ml receiving flask is prepared for the spinning band column by adding about 15 mg of hydroquinone and 20 drops of 85% phosphoric acid. All joints of the spinning band column are greased with high vacuum grease to assure a good vacuum seal. When assembled, insert the glass temperature probe into the 10/15 joint of the flask and insert the metal Tempora probe into the glass probe. Grease the 29/42 joint, containing the stopcock, into the flask and connect the sulfur dioxide gas line. The system is carefully placed under high vacuum to less than 0.5 Torr. The distillation on the spinning band is carried out according to the following conditions.

a. To begin the distillation, start the water cooler and adjust the cooling temperature to 15° C. Set the micro processor as follows to set up the memory for data input.
   1) System On "Select a Command Key"
   2) Press modify "Enter access code"
   3) 0000 "Enter"
   4) Modify Run "Select 10–19 (2)"
   5) Modify Run "then to 14"
Program

| | |
|---|---|
| 1) Enter name or number of run: | |
| 2) Enter mantle rate: | 25 volts |
| 3) Enter motor on temperature: | 24° C. |
| 4) Enter equilibration time: | 2 minutes |
| 5) Open temperature: | 28° C. |
| 6) Close temperature: | 90° C. |
| 7) Enter mantle rate: | 24° C. |
| 8) Enter reflux rate: | 20 to 1 |
| 9) Enter pot temperature to end run: | 90° C. |

A small flow of sulfur dioxide is leaked into the system. The leak is detected and controlled with the gas flow gauge, but it must be so small that the pressure of the system is not effected. The microprocessor is set to run the procedure. About 1 hour is required for the system to warm enough to heat the top of the distillation head. At the point of equilibration, when the head temperature is reading about 15 to 20° C. more than the pot, the cutting procedure begins after the equilibration is reached in about 10 minutes more. About 250±10 ml of the distillate is collected. The pot temperature should not be allowed to exceed 100° C. When the pressure reading is 1 Torr, the temperature of the distillation will be 57 to 58° C. The spinning band apparatus is allowed to cooled down (about 30 minutes). A 2 liter round-bottom flask, 24–40 ground glass jointed flask is acid washed, and is configured for high vacuum distillation. The flask is set up for magnetic stirring and equipped with a fraction cutter, a 10" Vigreux column, condenser, Claisen head and thermometer, all which have been acid washed. The residue remaining in the pot of the spinning band apparatus is poured into the 2 liter flask of the vacuum distillation apparatus. About 25 mg of hydroquinone and 25 drops of 85% phosphoric acid is added into the flask containing the residue. The pressure of the vacuum distillation apparatus is reduced to less than 1 Torr, and the residue is stirred. A small leak of sulfur dioxide is injected into the main pot as the distillation continues. The forecut receiver is prepared by adding approximately 10 mg of hydroquinone and 20 drops of 85% phosphoric acid. The forecut receiver is attached to the vacuum distillation and 75 ml of forecut is collected at a rate of 2 to 3 drops/minute. The main cut receiver is prepared by adding 5 to 15 mg of hydroquinone, 5 to 15 mg of p-methoxyphenol and 30 to 80 mg of pure crystalline phosphoric acid into a 2-liter round bottom receiving flask. The main receiver is attached to the vacuum distillation system without breaking the vacuum of the overall system. The total distillation will require 4 to 5 hours to complete. The distillation product, n-hexyl cyanoacrylate is analyzed for purity by gas chromatography. Ten grams of the n-hexyl cyanoacrylate is placed into a small weighing bottle. To this sample is added 1 drop of 1-hexanol. The net weight gained after each addition to the weighing bottle is noted so that the PPM of 1-hexanol in the chromatographic sample can be determined. The gas chromatograph instrument conditions are as follows:

| | |
|---|---|
| Instrument Description: | HP 5890 Gas Chromatograph with HP Chemstation Software |
| Column Description: | Supelco Nukol (60 meter, I.D.-0.32 mm, film thickness 1 micron |
| Instrument Parameters: | Method 1 |
| Injector Temperature: | 220° C. |
| Detector Temperature: | 280° C. |
| Head Pressure: | 15 PSI |
| Air Pressure: | 35 PSI |
| Hydrogen Pressure: | 40 PSI |
| Aux: | 60 PSI |
| Initial Oven Temperature: | 140° C. for 20 minutes |
| Ramp: | 5° C./minute |
| Final Oven Temperature: | 200° C. for 50 minutes |
| A Splitless System | |
| Injection Volume: | 1.0 micro liter |

If the distillate is insufficiently pure, the spinning band and vacuum distillation procedures are repeated.

Example 11

Purification of n-Hexyl Cyanoacrylate by Zone Melting

The following is a scaled up procedure that can be used for purifying manufacturing quantities of n-hexyl cyanoacrylate.

In a controlled temperature area, an exchange apparatus is attached to a flask containing the n-hexyl cyanoacrylate to be purified with the reserve flask attached to the other end of the exchange apparatus. The pressure in the assembly is lowered to less than 1 Torr. The temperature is maintained at −18±0.5° C. The assembly is allowed to equilibrate to the temperature for 24 hours. After 24 hours, touch or shake the n-hexyl cyanoacrylate gently, if it does not crystallize, repeat the procedure every 15 minutes for 1 hour. If the solution does not crystallize after 1 hour, take a small piece of dry ice and touch it to the side of the flask for 30 seconds. Once the crystallization begins, raise the temperature of the environment to −16.5±0.5° C. Allow the solution to sit undisturbed for 48 hours, while the crystallization goes to completion.

Reverse the position of the apparatus so that the liquid from the crystallization runs into the reserve flask. This should take 30 minutes to complete the draining. Keep the assembly in the controlled environment while the draining is being completed. The stopcock between the main flask and the reserve flask is closed to isolate the crystals. Allow air into the assembly on the side of the liquid through a drying tube and remove the liquid from the assembly. Allow air into the assembly through a drying tube. The assembly with the crystals are placed on the bench top and allowed to warm to room temperature and melt. The melted crystals are analyzed for purity. The purification procedure removed all of the inhibitors. The melted crystals are weighed to determine the amount of inhibitors to add. From the weight of the n-hexyl cyanoacrylate, the amount of the inhibitors that is added is determined according to these proportions relative to the amount of n-hexyl cyanoacrylate present, 100 PPM of hydroquinone, 100 PPM of p-methoxyphenol and 200 PPM of acetic acid.

The zone melting process is repeated a second time as follows. In a controlled temperature area, an exchange apparatus is attached on a flask containing the n-hexyl cyanoacrylate to be purified with the reserve flask attached to the other end of the exchange apparatus. The pressure in the assembly is lowered to less than 1 Torr. The temperature is maintained at −17±0.5° C. The assembly is allowed to equilibrate to the temperature for 24 hours. After 24 hours, touch or shake the n-hexyl cyanoacrylate gently, if it does not crystallize, repeat the procedure every 15 minutes for 1 hour. If the solution does not crystallize after 1 hour, take a small piece of dry ice and touch it to the side of the flask for 30 seconds. Once the crystallization begins, raise the temperature of the environment to −16.5±0.5° C. Allow the solution to sit undisturbed for 48 hours, while the crystallization goes to completion.

Reverse the position of the assembly so that the liquid from the crystallization runs into the reserve flask. This should take 30 minutes to complete the draining. Keep the assembly in the controlled environment while the draining is being completed. The stopcock between the main flask and the reserve flask is closed to isolate the crystals. Allow air into the assembly on the side of the liquid through a drying tube and remove the liquid from the assembly. Allow air into the assembly through a drying tube. The assembly with the crystals are placed on the bench top and allowed to warm to room temperature and melt. The melted crystals are analyzed for purity. The purification procedure removed all of the inhibitors. The melted crystals are weighed to determine the amount of inhibitors to add to the crystals. From the weight of the n-hexyl cyanoacrylate, the amount of the inhibitors that is added is determined according to these proportions relative to the amount of n-hexyl cyanoacrylate present, 100 PPM of hydroquinone, 100 PPM of p-methoxyphenol and 200 PPM of acetic acid.

Example 12

Preparation of Methyl Cyanoacrylate

The following is a scaled up procedure that can be used for preparing manufacturing quantities of n-hexyl cyanoacrylate. This prospective procedure is based on a smaller scale laboratory bench top synthesis used for preparing n-hexyl cyanoacrylate, and procedures developed employed for preparing 2-hexyl cyanoacrylate, as were taught in the preceding examples.

Equip a 5 liter three-necked flask with a reflux condenser, Dean-Stark trap, an addition funnel and a mechanical stirrer with a glass paddle in a 5 liter heating mantle. To the flask is added the following ingredients, 136.0±1.0 g (4.56 moles) of powdered paraformaldehyde, 136.0±1.0 g (4.56 moles) of prills of paraformaldehyde and 2,500±5 ml of methanol. The reaction mixture is stirred and heated to reflux. The reflux is continued until the solution becomes clear. Add 3 ml of piperidine to the refluxing mixture and wash into the reaction mixture with methanol from the reaction. Begin adding drop wise 9.1 g of methyl cyanoacetate. Turn down the heat to the reaction flask. The reaction is exothermic and the rate of addition should be adjusted to keep the reaction mixture at reflux temperature. The addition will take 45 minutes to one hour and will be more rapid near completion to the reaction. After completion of the addition, continue to reflux for 30 minutes. Collect the methanol distilled from the reaction flask through the Dean-Stark trap. Measure the amount recovered. Continue the reaction until 95% or more of the original volume of methanol is recovered.

The residues are collected in a 500 ml round bottom 24/40 ground glass jointed flask on the vacuum apparatus to collect the residues. The apparatus is placed under reduced pressure to continue to remove volatile materials. The procedure is continued until all water and organic condensate is removed from the mixture. The pressure is gradually reduced further until the pressure is less than 10 Torr. Heat is applied until hot to the touch, or all the solvent is removed. The heat is removed and the solution is allowed to cool. Add 25 to 30 g of phosphorous pentoxide through a powder funnel into the distillation flask. After completion of the addition of phosphorous pentoxide, close the apparatus at once in order to minimize the exposure of the phosphorous pentoxide to air. The heat is turned off and the mixture is allowed to stir for one hour. After one hour, the apparatus is flooded with sulfur dioxide.

The pressure in the apparatus is reduced to less than 10 Torr, and heat is slowly applied. The system is flooded with sulfur dioxide and the stirring is maintained.

A 1 liter flask is prepared as a receiver by acid washing. Add 10 drops of 85% phosphoric acid and approximately 25 to 50 mg of hydroquinone. This receiver flask is attached to the distillation apparatus without breaking vacuum. Heat and stir the hot cracking reaction until distillation begins. Collect 800 to 1200 g of product. The crack reaction will require about 3 to 4 hours. Discontinue the distillation of the product when the temperature begins to rise past 110° C.

The purity of the methyl cyanoacrylate is determined by gas chromatography under the following conditions.

| | |
|---|---|
| Instrument Description: | HP 5890 Gas Chromatograph with HP Chemstation Software |
| Column Description: | Supelco Nukol (60 meter, I.D.- 0.32 mm, film thickness 1 micron |
| Instrument Parameters: | Method 1 |
| Injector Temperature: | 220° C. |
| Detector Temperature: | 280° C. |
| Head Pressure: | 15 PSI |
| Air Pressure: | 35 PSI |
| Hydrogen Pressure: | 40 PSI |
| Aux: | 60 PSI |
| Initial Oven Temperature: | 140° C. for 20 minutes |
| Ramp: | 5° C./minute |
| Final Oven Temperature: | 200° C. for 50 minutes |
| A Splitless System | |
| Injection Volume: | 1.0 micro liter |

Example 13

Purification of Methyl Cyanoacrylate by Zone Melting

The following is a scaled up procedure that can be used for purifying manufacturing quantities of methyl cyanoacrylate.

In a controlled temperature area, an exchange apparatus is placed on a flask containing the methyl cyanoacrylate to be purified with the reserve flask attached to the other end of the exchange apparatus. The pressure in the assembly is lowered to less than 1 Torr. The temperature is maintained at 3 to 5° C. The assembly is allowed to equilibrate to the temperature for 24 hours. After 24 hours, touch or shake the methyl cyanoacrylate gently, if it does not crystallize, repeat the procedure every 15 minutes for 1 hour. If the solution does not crystallize after 1 hour, take a small piece of dry ice and touch it to the side of the flask for a few seconds. Once the crystallization begin, allow the solution to sit undisturbed for 24 hours, while the crystallization goes to completion.

Reverse the position of the assembly so that the liquid from the crystallization runs into the reserve flask. This should take about 15 minutes to complete the draining. Keep the assembly in the controlled environment while the draining is being completed. The stopcock between the main flask and the reserve flask is closed to isolate the crystals. Allow air into the assembly on the side of the liquid through a drying tube and remove the liquid from the assembly. Allow air into the remainder of the assembly through a drying tube. The assembly with the crystals are placed on the bench top and allowed to warm to room temperature and melt. The melted crystals are analyzed for purity. The weight of the melted crystals is taken to determine the amount of inhibitors to add to the crystals. The purification procedure removes all of the inhibitors and the inhibitors are needed to maintain the stability of the methyl cyanoacrylate. From the weigh of the methyl cyanoacrylate, the amount of the inhibitors to added is determined according to the following portions relative to the amount of methyl cyanoacrylate, 100 PPM of hydroquinone, 100 PPM of p-methoxyphenol and 200 PPM of acetic acid.

The zone melting process is repeated a second time as follows. In a controlled temperature area, an exchange apparatus is placed on a flask containing the methyl cyanoacrylate to be purified. The pressure in the overall assembly is lowered to less than 1 Torr. The temperature is maintained at 3 to 5° C. The apparatus is allowed to equilibrate to the temperature for 24 hours. After 24 hours, touch or shake the methyl cyanoacrylate gently, if it does not crystallize, repeat the procedure every 15 minutes for 1 hour. If the solution does not crystallize after 1 hour, take a small piece of dry ice and touch it to the side of the flask for 30 seconds. Once the crystallization begins allow the solution to sit undisturbed for 24 hours, while the crystallization goes to completion.

Reverse the position of the apparatus so that the liquid from the crystallization runs into the reserve flask. This should take 5 to 10 minutes to complete the draining. Keep the assembly in the controlled environment while the draining is being completed. The stopcock between the main flask and the reserve flask is closed to isolate the crystals. Allow air into the assembly on the side of the liquid through a drying tube and remove the liquid from the apparatus. Allow air into the assembly through a drying tube. The assembly with the crystals are placed on the bench top and allowed to warm to room temperature and melt. The melted crystals are analyzed for purity. The purification procedure removed all of the inhibitors. The weight of the melted crystals is taken to determine the amount of inhibitors to add to the crystal. From the weigh of the n-hexyl cyanoacrylate, the amount of the inhibitors is calculated as such, 100 PPM of hydroquinone, 100 PPM of p-methoxyphenol and 200 PPM of acetic acid.

Example 14

Formulation of a Monomer Component with n-Hexyl Cyanoacrylate

The following is a scaled up procedure that can be used for preparing manufacturing quantities of Polymer A, also known as, Neuracryl A. This prospective procedure is based on a smaller scale laboratory bench top synthesis used for preparing the monomer component, and procedures developed employed for preparing Polymer M, also known as Neuracryl M, as were taught in the preceding examples.

A. A monomer component with n-hexyl cyanoacrylate is formulated with the following materials, n-hexyl cyanoacrylate, hydroquinone, p-methoxyphenol and glacial acetic acid. The hydroquinone and p-methoxyphenol are kept under reduced pressure in a desiccator over a drying agent. The glacial acetic acid is taken up in a syringe and the syringe and the inhibitor is weighed, an amount of glacial acetic acid is added, and the syringe with the glacial acetic acid is re-weigh to determine the amount of glacial acetic acid that had been added. This process is repeated until the desired amount of glacial acetic acid is added.

The monomer component is analyzed by gas chromatography for purity under the following conditions.

Instrument Description: HP5890 Gas Chromatograph with HP chemstation software.

| Column Description: | Supelco Nukol (60 meters-length, I.D., 0.32 mm, Film Thickness 1 micron) |
|---|---|
| Instrument Parameters: | Method 1 |
| Injector Temperature: | 220° C. |
| Detector Temperature: | 280° C. |
| Head Pressure: | 15 PSI |
| Air Pressure: | 35 PSI |
| Hydrogen Pressure: | 40 PSI |
| Aux: | 60 PSI |
| Initial Oven Temperature: | 140° C. for 20 min. |
| Ramp: | 5° C./min. |
| Final Oven Temperature: | 200° C. for 50 min. |
| A Splitless System. | |
| Injection Volume: | 1.0 microliter |

The component is sufficient pure if the combined impurities present totals to less than 1%.

B. Following the procedures taught in Part A of the present Example, a monomer component with a combination of methyl cyanoacrylate and n-hexyl cyanoacrylate can be made.

In place of the amount of n-hexyl cyanoacrylate called for in the above procedure, a combination of methyl cyanoacrylate and n-hexyl cyanoacrylate is use. The amounts of each material used is determined according to the following ratio:

moles of methyl cyanoacrylate=0.111×moles n-hexyl cyanoacrylate

Example 15

The Behavior of Neuracryl M in the Pig Rete

This example compares the intravascular behavior of Neuracryl M to the current clinical standard, n-butyl cyanoacrylate 40% in the rete of the pig.

Methods and Materials

Neuracryl M is available from Prohold Technologies, El Cajon, Calif. Neuracryl M is a two-part embolization agent consisting of a glass ampule of 1.25 ml Neuracryl M1 and a rubber-stoppered glass vial of Neuracryl M2 (a mixture of 2-hexyl cyanoacrylate, an esterified fatty acid, and gold particles measuring approximately 5pm in diameter. Prior to use, the contents of the Neuracryl M1 vial are injected into the vial containing Neuracryl M2, and the two are shaken together thoroughly until mixed. The gold particles and esterified fatty acid are used to retard polymerization and provide radiopacity. To avoid separation of the components or contamination, the two moieties were not mixed until immediately before use. NBCA (Histacryl Blue) was obtained from B. Braun, Melsungen, Germany, and mixed with Ethiodol to form a 40% solution.

Nine barnyard pigs were placed under general anesthesia. Using sterile technique a catheter was placed in the right femoral artery and a guiding catheter in the left common artery. A microcatheter was introduced into the region of the rete, through which the entire cerebral blood passes.

With the pigs under general endotracheal anesthesia, using sterile technique, the right femoral artery was catheteried and a guiding catheter was placed into the left common carotid artery of nine pigs. A microcatheter was introduced into the region of the rete, and 0.1 to 0.3 of NBCA (n-butyl cyanoacrylate) or Neuracryl M was infused without flow arrest. After follow-up angiography, the opposite carotid and pharyngeal arteries were catheterized, and the alternative agent was infused. One pig was sacrificed immediately, six were sacrificed at 3 weeks, and two were sacrificed at 3 months.

Results

One pig was sacrificed immediately due to clinical infarction. Distal embolization of NBCA was found to be the cause.

In one pig (sacrificed immediately because of clinical infarction), distal embolization of the NBCA was found. In the other pigs, penetration of the embolic agent into the rete was graded as follows, 0, no penetration; 1, penetration of 25% or less; 2, 25–50% penetration; 3, 50–75% penetration; and 4, 75–100% penetration.

Summary of the Results

| Material | Penetration mean | Catheter Trapped | Embolization Distal to Rete |
|---|---|---|---|
| Neuracryl M | 3.7 | 0/9 | 0/9 |
| NBCA | 1.8 | 4/9 | 2/9 (one death) |

Neuracryl M had a mean penetration grade of 3.7, compared to 1.8 for NBCA. Trapping of the catheter by the glue mass occurred in four of nine pigs with NBCA, whereas there were no occurrences in the pigs treated with Neuracryl M. Embolization occurring distal to the rete occurred in two pigs infused with NBCA, with one resultant death. There were no occurrences of embolization occurring distal to the rete in pigs infused with Neuracryl M.

| Material | Intraluminal | Mural | Perivascular | Interstitial | Giant Cells |
|---|---|---|---|---|---|
| Inflammation at 3 weeks (6 pigs) | | | | | |
| Neuracryl M | 1.9 | 2.2 | 2.0 | 1.0 | 5/7 |
| NBCA | 0.6 | 0.8 | 0.8 | 0.2 | 2/7 |
| Inflammation at 3 months (2 pigs) | | | | | |
| Neuracryl M | 3.0 | 3.0 | 3.0 | 0.3 | 2/2 |
| NBCA | 1.5 | 1.5 | 1.5 | 0.3 | 2/2 |

An initial inflammatory response is the essential initiator of the healing process, and leads to fibroblastic ingrowth. If the inflammatory response is excessive, pus is produced. Too little response, and no scar, or only temporary occlusion occurs. The Neuracryl M yielded a consistently greater inflammatory response than the present clinical standard, NBCA.

Conclusion

Neuracryl M compares favorably with NBCA, showing greater penetration into the rete of the pig while being less likely to cause catheter trapping or distal embolization.

Example 16

Comparison of Cyanoacrylate Compositions for Conformal Eendovascular Obliteration Utility The endovascular treatment of cerebral berry aneurysms has improved over the last decade, but aneurysms with wide necks or having shapes other than spherical remain technically challenging. An ideal device would, when delivered, conform exactly to the aneurysm lumen, stay together as a cohesive whole, reestablish the contours of the parent vessel, and be permanent. We report initial experiments modifying cyanoacrylate monomers to develop such a device.

Methods and Materials

Transparent silicone models of aneurysms representing both narrow and wide neck configurations were constructed. Model A consisted of a straight 4 mm tube with three 7 mm aneurysms attached. The neck diameter was 3 mm. Model B consisted of a helical 4 mm tubing containing four aneurysms positioned along the greater curvature. Two were 5 mm in diameter (1 having a 2 mm neck, and the other having a 4 mm neck), and two were 9 mm in diameter (1 having a 3 mm neck, and the other a three by 5 mm neck). The helical model ended in a bifurcation; a 4 mm wide neck aneurysm was positioned at the bifurcation to simulate a basiler tip aneurysm.

Twelve compounded cyanoacrylates were tested, six based upon the 2-hexyl cyanoacrylate monomer, six based upon the 1-hexyl cyanoacrylate monomer. Additives consisted of various oils, gold for opacification, and polymerization retardants. The silicone aneurysms were filled with heparinized pig blood, and were injected with microcatheters under direct visualization during static conditions, and under fluoroscopic guidance during pulsatile flow conditions.

Model A was filled with heparinized pig blood, and each of the twelve compounds was injected into three aneurysms, directly visualizing the degree of filing. The models were then radiographed, opened, and the contents examined by microscopy.

Model B was perfused with heparinized pig blood, pulsatile flow, 40 centimeters per second. The mixtures were introduced via micro-catheters; injection was controlled with fluoroscopic visualization.

Results

All twelve mixtures remained cohesive and conformed nicely to the outline of the aneurysm. Many of the mixtures based upon the 2-hexyl monomer exhibited delayed polymerization,and could not be kept witin the aneurysm lumen, even with adjacent balloon control of the infusion process. Four of the mixtures based upon the 1-hexyl monomer gave good cohesion, good conformation, remained within the aneurysm, and allowed some degree of angioplasty and remodeling of the arterial lumen by silicone balloon.

Conclusion

Several of the cyanoacrylate mixtures show promise as a liquid embolic agent to treat berry aneurysms by direct injection through microcatheters.

Example 17

Clinical Trial Comparing Neuracryl M to PVA Foam

This example reports the results of a randomized clinical trial with 12 patients comparing Neuracryl M and PVA Foam.

Materials and Methods

The procedure for the clinical study was conducted under the purview of the FDA and within approved institutional guidelines. Twelve pre-surgical patients satisfied the criteria to enter the study. After angiographic evaluation and randomization (75 percent to Neuracryl M/25 percent to PVA form according to the FDA recognized standard). Ten patients were treated using standard micro-catheter technique with Neuracryl M; and two were treated with PVA. Patients were subsequently operated upon, and any residual nidus was removed. The angiograms were analyzed by three independent observers who compared the area of the nidus both before and after treatment in both AP and lateral planes.

Results

No patient's condition worsened clinically. Of the two who randomized to PVA, one showed an 81 percent reduction in nidus size; the second had no significant change in nidus size. Of the ten who randomized to Neuracryl M, 5 were angiographically obliterated (using measurement criteria submitted to the FDA), 2 had nidus size reduction between 50 and 99 percent, 2 were obliterated less than 50 percent, and one nidus was judged to have actually enlarged by 25 percent. No catheter was glued in place.

Conclusion

Neuracryl M provides a better angiographic obliteration rate than the historical standard, PVA form particles, and a better obliteration rate than the literature reports of patients treated with Histoaryl. In the patient whose AVM appeared to enlarge, the Neuracryl M slowed flow through the lesion sufficiently to make it more conspicuous and thus easier to measure.

Example 18

Initial Neuropathologic Observation after Treatment of a Human Arteriovenous Malformation with Neuracryl M This example reports the treatment of a 34 year old male presented after acute hemorrhage of a right parieto-occipital arteriovenous malformation (AVM). The pathologic features of the AVM after embolization with Neuracryl M.

Materials and Methods

Transcatheter embolization was performed on post-bleed day 21 using a novel, proprietary cyanoacrylate-based compound, Neuracryl M. Four days after embolization, the patient underwent surgical resection.

Results

Scattered foci of Neuracryl M completely contained within vessels were observed. Embolic material formed a lamellar, spongiform configuration, was non-polarizable, and stained moderately eosinophilic with hematoxylin and eosin. A profound acute inflammatory response was seen surround many of the AVM vessels, including frank necrosis and giant cell foreign body reaction.

Conclusion

Neuracryl M was an effective embolic agent which was retained within vessel lumina and initiated a marked localized inflammatory reaction by 4 days. This report represents the initial pathologic observations of Neuracryl M in the first human subject treated. As further specimens are obtained, a more complete description of the behavior of Neuracryl M in the human brain will emerge.

We claim:

1. A composition comprising a combination of:
   a monomer component comprised of 2-hexyl cyanoacrylate, and at least one inhibitor; and
   a second component comprised of an alkyl cyanoacrylate polymer, an alkyl esterified fatty acid and an opacifying agent,
   wherein said composition forms a resultant aggregate structure when said composition contacts an anionic environment.

2. The composition of claim 1, wherein said monomer component has at least two inhibitors.

3. The composition of claim 1, wherein said monomer component has at least three inhibitors.

4. The composition of claim 3, wherein said three inhibitors are hydroquinone, p-methoxyphenol and phosphoric acid.

5. The composition of claim 1, wherein the at least one inhibitor is hydroquinone.

6. The composition of claim 5 wherein hydroquinone is in the range of about 50 to 150 parts per million.

7. The composition of claim 5, wherein hydroquinone is in the range of about 95 to 105 PPM.

8. The composition of claim 1, wherein the at least one inhibitor is p-methoxyphenol.

9. The composition of claim 8, wherein p-methoxyphenol is in the range of about 50 to 150 PPM.

10. The composition of claim 8, wherein p-methoxyphenol is in the range of about 75 to 125 PPM.

11. The composition of claim 8, wherein p-methoxyphenol is in the range of about 95 to 105 PPM.

12. The composition of claim 1, wherein the at least one inhibitor is phosphoric acid.

13. The composition of claim 12, wherein phosphoric acid is in the range of about 125 to 375 PPM.

14. The composition of claim 12, wherein phosphoric acid is in the range of about 187.5 to 312.5 PPM.

15. The composition of claim 12, wherein phosphoric acid is in the range of about 200 to 300 PPM.

16. The composition of claim 1, wherein said alkyl esterified fatty acid is selected from the group consisting of alkyl laurate, alkyl palmitate and stearic alkyl myristate.

17. The composition of claim 1, wherein said alkyl esterified fatty acid is ethyl myristate.

18. The composition of claim 1, wherein said opacificant agent is selected from group consisting of gold, platinum, tantalum, titanium, tungsten and barium sulfate.

19. The composition of claim 18, wherein said opacificant agent is gold.

20. The composition of claim 19, wherein said gold is in fine powder form with individual particles no larger than about 7 microns in diameter.

21. The composition of claim 19, wherein said gold is in fine powder form with individual particles no larger than about 5 microns in diameter.

22. The composition of claim 19, wherein said gold is in fine powder form with individual particles no larger than about 2 microns in diameter.

23. The composition of claim 19, wherein said gold is in fine powder form with individual particles no larger than about 1 micron in diameter.

24. A composition comprising a combination of:
- a monomer component comprised of poly(2-hexyl cyanoacrylate), hydroquinone, p-methoxyphenol, and phosphoric acid; and
- a second component comprised of 2-hexyl cyanoacrylate, ethyl myristate and gold, wherein said composition forms a resultant aggregate structure when said composition contacts an anionic environment.

25. A composition comprising a monomer component comprising a combination of:

2-hexyl cyanoacrylate, at least one inhibitor; and a second component that functions as an opacifying agent; wherein said composition forms a resultant aggregate structure when said composition contacts an anionic environment.

26. The composition of claim 25, wherein said second component is a halogenated oil.

27. The composition of claim 25, wherein said second component is 37% iodine by weight, covalently linked to poppy seed oil.

28. A composition comprising a monomer component comprised of 2-hexyl cyanoacrylate and hydroquinone, p-methoxyphenol, and phosphoric acid, and 37% iodine by weight, covalently linked to poppy seed oil.

29. A method of filling, occluding, partially filling or partially occluding an unfilled volume or space in a mass in an anionic environment comprising administering a composition of claim 1.

30. The method of claim 29, wherein said space is an existing space in the body.

31. The method of claim 30, wherein said existing space is a lumen of a passageway in the body.

32. The method of claim 30, wherein said existing space is a blood vessel.

33. The method of claim 30, wherein said existing space is a duct.

34. The method of claim 29, wherein said space is created by a transiently placed external device.

35. The method of claim 29, wherein said space is created or resulting from a procedure.

36. The method of claim 29, wherein said space is created by the placement or implantation of an object.

37. The method of claim 29, wherein said space is created by the composition itself.

38. A method of ablating diseased or undesired tissue by cutting off the blood supply to said tissue, comprising administering a composition of claim 1 to the blood vessel(s) that feed said tissue, where said blood vessel(s) are occluded thereby cutting off the blood supply to said tissue.

39. The method of claim 38, wherein said undesired tissue is an arteriovenous venous malformation.

40. The method of claim 38, wherein said undesired tissue is a tumor.

41. The method of claim 38, wherein said undesired tissue is an uterine leiomyoma.

42. A method of treating arteriovenous venous malformation ("AVM") comprising administering a composition of claim 1 to the blood vessel(s) that feed said AVM, where said blood vessel(s) are occluded thereby cutting off the blood supply to said AVM.

43. A method of treating a tumor comprising administering a composition of claim 1 to the blood vessel(s) that feed said tumor, where said blood vessel(s) are occluded thereby cutting off the blood supply to said tumor.

44. A method of treating an uterine leiomyoma comprising administering a composition of claim 1 to the blood vessel(s) that feed said uterine leiomyomas, where said blood vessel(s) are occluded thereby cutting off the blood supply to said uterine leiomyoma.

45. A method of sterilizing a female mammal comprising administering a composition of claim 1 to the fallopian tubes thereby preventing the passage of the eggs from the ovaries to the uterus of said female mammal.

* * * * *